United States Patent
Williams et al.

(10) Patent No.: US 8,173,445 B1
(45) Date of Patent: May 8, 2012

(54) DNA INTERCALATING AGENTS

(75) Inventors: John G. K. Williams, Lincoln, NE (US); Daniel R. Draney, Lincoln, NE (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 430 days.

(21) Appl. No.: 12/263,386

(22) Filed: Oct. 31, 2008

Related U.S. Application Data

(62) Division of application No. 11/338,990, filed on Jan. 24, 2006, now Pat. No. 7,462,468.

(60) Provisional application No. 60/648,091, filed on Jan. 28, 2005.

(51) Int. Cl.
  *G01N 33/53* (2006.01)
  *C07H 21/02* (2006.01)
  *C12Q 1/68* (2006.01)
  *C12P 19/34* (2006.01)

(52) U.S. Cl. ......... 436/800; 536/25.32; 435/6; 435/91.1

(58) Field of Classification Search .................. 436/800; 536/25.32; 435/6, 91.1
See application file for complete search history.

(56) References Cited

U.S. PATENT DOCUMENTS

| | | | |
|---|---|---|---|
| 5,410,030 | A | 4/1995 | Yue et al. |
| 5,582,977 | A | 12/1996 | Yue et al. |
| 5,863,753 | A | 1/1999 | Haugland et al. |
| 6,664,047 | B1 | 12/2003 | Haugland et al. |
| 7,462,468 | B1 | 12/2008 | Williams et al. |

OTHER PUBLICATIONS

Carreon et al. (Organic Letters 2004, 6, No. 4, 517-519).*
Atwell et al. J. Med. Chem. 1986, 29 pp. 69-74.*
Rye, et al.; Stable fluorescent complexes of double-stranded DNA with bis-intercalating asymmetric cyanine dyes: properties and applications; *Nucleic Acids Research*; Feb. 1992; vol. 20, No. 11, Previously presented. 2803-2812.
Seeman, N. C.; At the Crossroads of Chemistry, Biology and Materials: Structural DNA Nanotechnology; *Chemistry & Biology*; 2003, vol. 10, 1151-1159.
Choi, Y., et al.; Synthesis and Functional Evaluation of DNA-Assembled Polyamidoamine Dedrimer Clusters for Cancer Cell Specific Targeting; *Chemistry & Biology*; 2005; vol. 12, 35-43.

* cited by examiner

*Primary Examiner* — Jezia Riley
(74) *Attorney, Agent, or Firm* — Robert H. Reamey

(57) ABSTRACT

The present invention provides compositions and methods for detecting incorporation of a labeled nucleotide triphosphate onto the growing end of a primer nucleic acid molecule. The method is used, for example, to genotype and sequence a nucleic acid. In a preferred embodiment, the method described herein detects individual NTP molecules.

12 Claims, 16 Drawing Sheets

A DNA Nanoparticle Stainable By Dyes Of The Present Invention

> Duplex of nts 1-729 (Main_Translate.vi, aminoAcidsPerOutputRow=27)

```
CGGACGCAAAGCATGCACCCAGCCAAATTCACAAGGCGAT  GACCACGCCACCCGCCTAGCCGTATAACGAAGCGAACAACG                                StartA, StartB
  -------+---------+---------+---------+  ---------+---------+---------+---------+
GCCTGCGTTTCGTACGTGGGTCGGTTTAAGTGTTCCGCTA.CTGGTGCGGTGGGCCGGATCGGCATATTGCTTGCTTGTTGC  ⎫
                                                                                  ⎬  Ring1
ATGCATGTAGTCTGAAATGAACATGAGCAATGAGGCGCGG AATCAACAAAGTCACCAGGATCACACGGCAAATACATAGGC  ⎭
  -------+---------+---------+---------+  ---------+---------+---------+---------+
TAGCTACATCAGACTTTACTTGTACTCGTTAGCTCCGCGC.TTAGTTGTTTCAGTGGTCCTAGTGTGCCGTTTATGTATCCG  ⎫
                                                                                  ⎬  Ring2
CGGGCATTCAGCTGACCATGGGCGCTACAATCACCTAC  AGATAAGACAACACAACAACTTGAGGTCCATCTAGCAACTCAAG ⎭
  -------+---------+---------+---------+  ---------+---------+---------+---------+
GCGCCGTAAGTCGACCTGGTACCCGCGATGTTAGTGGATG.TCTATTCTGTTGTGTTGAACTCCAGGTAGATCGTTGAGTTC  ⎫
                                                                                  ⎬  Ring3
ACCCAATAACACCGAGATCGCCCTAAGGTCTAGTCATAT  CACGAGCTGTAATAAATAGCGTATCCAAATGCTAACTTATA   ⎭
  -------+---------+---------+---------+  ---------+---------+---------+---------+
TGGGTTATTGTGGCTCTAGCGGGACATTCCAGATCAGTATA.GTGCTCGACATTATTTATCGCATAGGTTTACGATTGAATAT ⎫
                                                                                  ⎬  Ring4
ATGACGAACGCGATAAGGCATTAAAATGTCCCGTTGCCATA ACCGCAGAACTATGACTAGAACGGACAGCTCCAGATGAATC ⎭
  -------+---------+---------+---------+  ---------+---------+---------+---------+
TACTGCTTGCGCTATTCCGTAATTTACAGGGCAACGGTAT.TGGCGTCTTGATACTTCCATTCTTGCCTGTCGAGCTCTACTTAG ⎫
                                                                                  ⎬  Ring5
CATCGGCCACAGGACCCTGTCCACTAGCGAGTCGAATTAA  CATATGCCGAAATGGCCAGCTAGGATTACGACGACTATCGA ⎭
  -------+---------+---------+---------+  ---------+---------+---------+---------+
GTAGCCGGTGTCCTGGGACAGGTGATCGCTCAGCTTAATT GTATACGGCTTTACCGGTCCATCCTAATGCTGCTGATAGCT  ⎫
                                                                                  ⎬  Ring6
AACGAGACTGATAACTGTACGGGCATTGCAAACGCACAGT  CCGACCGATGGTAAAGTTAGAATGTACATTGGATGCCAGA  ⎭
  -------+---------+---------+---------+  ---------+---------+---------+---------+
TTGCTCTGACTATTGACATGCGCGGTAACGTTTGCGTCTCA.GGCTGGCTACCCATTTCAATCTTACATGTAACCTACGGGTCT ⎫
                                                                                  ⎬  Ring7
CAGAGTGGACTTAAACTCGGCGGCCGGAACGGACCATCTCAATGTGA TCATGATGGAGTACCGAACCATATAGCCAGGTGCACCGAAC ⎭
  -------+---------+---------+---------+  ---------+---------+---------+---------+
GTCTCACCTGAATTTGAGCCGCGCCCTGGTAGAGTTACACT.AGTACTACCTCATGGCTTGGTATATCGGTCCACGTGCCTTG ⎫
                                                                                  ⎬  Ring8
CGACAAATTAGACTCACAGCGTCAGTGACAGTTCCATACC AACGCTCACTTAGATACAAACTGACAATGCGACTGGAATAC   ⎭
  -------+---------+---------+---------+  ---------+---------+---------+---------+
GCTGTTTAATCGAGTGTCGCAGTCACTGTCAAGGTATGG.TTGCGAGTGAATCTATGTTTGACTGTTACGCTGACCTTATG              End
```

Ring1: DNA nanoparticle constructed of eight complementary 170-mer oligonucleotides (Ring1-8), one 81-mer, one 41-mer (StartB) and one 40-mer (StartA). The underlined nucleotide letters are the 5'-end of each oligo; so each "Ring" type sequence should be read from the 5'-end continuously around the circle to the 3'-end (the 3' and 5' ends of a given oligo are thus juxtaposed in this drawing). Dash and plus characters indicate base pairing between complementary strands. Brackets represent four T's (dTp4) connecting contiguous sequences spanning two lines in the figure. Dots in the sequence strings represent placeholders to better align the displayed sequences (i.e. dots are not a nucleotide, not a strand break). Gaps (vertically aligned with the dots) represent strand breaks between the 5'- and 3'-ends of juxtaposed oligos. It is believed these physical breaks will promote more efficient staining with the dyes of the present invention, by allowing for topological relaxation.

FIG. 4

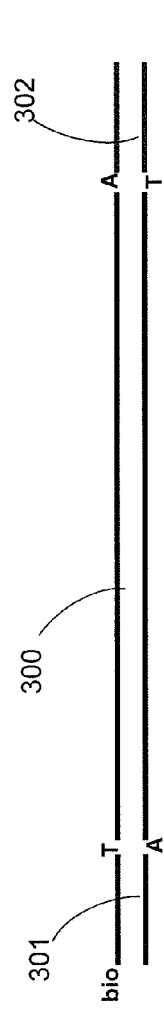
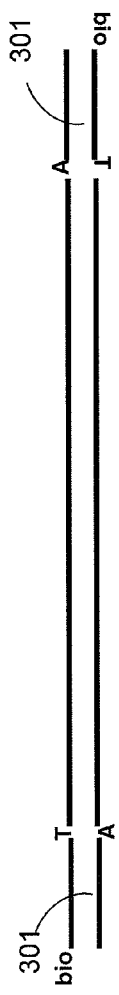
FIG. 8

Single Molecule Configuration
DNA-protein complexes
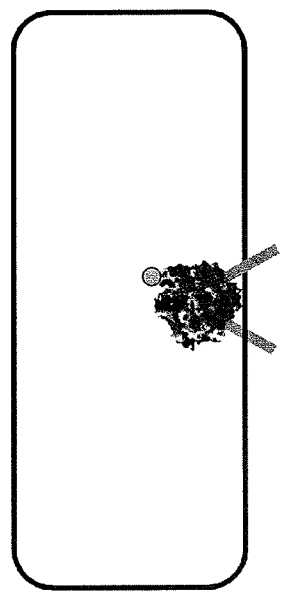
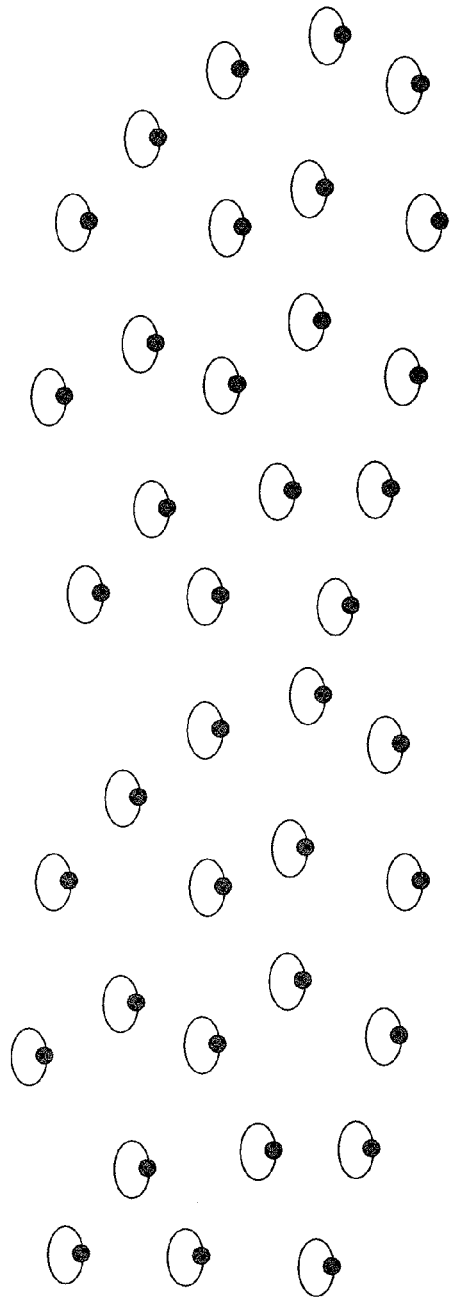
FIG. 11

DNA INTERCALATING AGENTS

CROSS-REFERENCE TO RELATED APPLICATIONS

This application is a divisional application of U.S. patent application Ser. No. 11/338,990, filed Jan. 24, 2006, which application claims the benefit of priority to U.S. Provisional Patent Application No. 60/648,091, filed Jan. 28, 2005, both of which are hereby incorporated in their entirety for all purposes.

STATEMENT AS TO RIGHTS TO INVENTIONS MADE UNDER FEDERALLY SPONSORED RESEARCH AND DEVELOPMENT

This invention was made with government support under Contract No. 1 R43 HG003610-01 awarded by the National Institutes of Health. The government has certain rights in the invention.

BACKGROUND OF THE INVENTION

The primary sequences of nucleic acids are crucial for understanding the function and control of genes and for applying many of the basic techniques of molecular biology. In fact, rapid DNA sequencing has taken on a more central role after the goal to elucidate the entire human genome has been achieved. DNA sequencing is an important tool in genomic analysis as well as other applications, such as genetic identification, forensic analysis, genetic counseling, medical diagnostics, and the like. With respect to the area of medical diagnostic sequencing, disorders, susceptibilities to disorders, and prognoses of disease conditions can be correlated with the presence of particular DNA sequences, or the degree of variation (or mutation) in DNA sequences, at one or more genetic loci. Examples of such phenomena include human leukocyte antigen (HLA) typing, cystic fibrosis, tumor progression and heterogeneity, p53 proto-oncogene mutations and ras proto-oncogene mutations (see, Gyllensten et al., PCR Methods and Applications, 1: 91-98 (1991); U.S. Pat. No. 5,578,443, issued to Santamaria et al.; and U.S. Pat. No. 5,776,677, issued to Tsui et al.).

Various approaches to DNA sequencing exist. The dideoxy chain termination method serves as the basis for all currently available automated DNA sequencing machines. (see, Sanger et al., Proc. Natl. Acad. Sci., 74: 5463-5467 (1977); Church et al., Science, 240: 185-188 (1988); and Hunkapiller et al., Science, 254: 59-67 (1991)). Other methods include the chemical degradation method, (see, Maxam et al., Proc. Natl. Acad. Sci., 74: 560-564 (1977), whole-genome approaches (see, Fleischmann et al., Science, 269, 496 (1995)), expressed sequence tag sequencing (see, Velculescu et al., Science, 270, (1995)), array methods based on sequencing by hybridization (see, Koster et al., Nature Biotechnology, 14, 1123 (1996)), and single molecule sequencing (SMS) (see, Jett et al., J. Biomol. Struct. Dyn. 7, 301 (1989) and Schecker et al., Proc. SPIE-Int. Soc. Opt. Eng. 2386, 4 (1995)).

U.S. Pat. No. 6,255,083, issued to Williams and incorporated herein by reference, discloses a single molecule sequencing method on a solid support. The solid support is optionally housed in a flow chamber having an inlet and outlet to allow for renewal of reactants that flow past the immobilized polymerases. The flow chamber can be made of plastic or glass and should either be open or transparent in the plane viewed by the microscope or optical reader.

U.S. Pat. No. 4,979,824, illustrates that single molecule detection can be achieved using flow cytometry wherein flowing samples are passed through a focused laser with a spatial filter used to define a small volume. Moreover, U.S. Pat. No. 4,793,705 describes a detection system for identifying individual molecules in a flow train of the particles in a flow cell. The patent further describes methods of arranging a plurality of lasers, filters and detectors for detecting different fluorescent nucleic acid base-specific labels.

Single molecule detection on a solid support is described in Ishikawa, et al. Jan. J. Apple. Phys. 33:1571-1576. (1994). As described therein, single-molecule detection is accomplished by a laser-induced fluorescence technique with a position-sensitive photon-counting apparatus involving a photon-counting camera system attached to a fluorescence microscope. Laser-induced fluorescence detection of a single molecule in a capillary for detecting single molecules in a quartz capillary tube has also been described. The selection of lasers is dependent on the label and the quality of light required. Diode, helium neon, argon ion, argon-krypton mixed ion, and Nd:YAG lasers are useful in this invention (see, Lee et al. (1994) Anal. Chem., 66:4142-4149).

The predominant method used today to sequence DNA is the Sanger method (Proc. Natl. Acad. Sci. 1977, 74, 5463) which involves use of dideoxynucleoside triphosphates as DNA chain terminators. Most high throughput-sequencing systems use this approach in combination with use of fluorescent dyes. The dyes may be attached to the terminator or be a part of the primer. The former approach is preferred as only the terminated fragments are labeled. Multiplexing energy transfer fluorescent dyes are preferable over the use of single dyes.

U.S. Pat. No. 6,306,607 describes modified nucleotides wherein the nucleotide has a terminally labeled phosphate, which characteristic is useful for single-molecule DNA sequencing in a microchannel. Using 4 different NTPs each labeled with a unique dye, real-time DNA sequencing is possible by detecting the released pyrophosphate having different labels. The cleaved PPi-Dye molecules are detected in isolation without interference from unincoporated NTPs and without illuminating the polymerase-DNA complex.

WO 04/092331 discloses compositions and methods for detecting the incorporation of labeled nucleotide phosphates onto the growing end of a primer nucleic acid molecule. The compositions and methods allow for increasing the processivity index of polymerases and thus, result in more efficient nucleic acid sequencing. The method is used, for example, to genotype and sequence a nucleic acid.

Despite the advances in WO 04/092331, a need exists for more effective and efficient compositions, methods, and systems for nucleic acid sequencing. Specifically, a need exists for improved substrates for polymerases and methods for sequencing. These and further needs are provided by the present invention.

SUMMARY OF THE INVENTION

In one embodiment, the present invention provides a compound of Formula I:

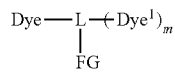

wherein: Dye is a monomeric or dimeric dye; $Dye^1$ is a monomeric dye; L is a covalent linkage; m is an integer from 0 to 4; and FG is a functional group selected from a reactive group, an activatable group, and a bio-moiety comprising a biomolecule.

In certain aspects, the compounds of Formula I, have Formula Ia:

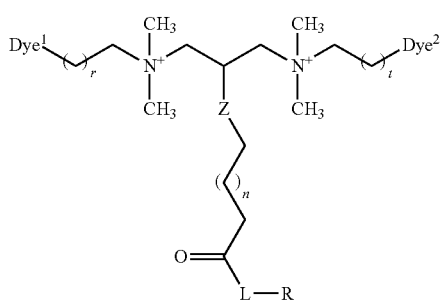

wherein: $Dye^1$ is selected from the group of TO-1, TO-3, BO-1, BO-3, YO-1, YO-3, JO-1, JO-3, PO-1, PO-3, LO-1, LO-3, YO-1, YO-3, propidium and psoralen. $Dye^2$ is selected from the group of TO-1, TO-3, BO-1, BO-3, YO-1, YO-3, JO-1, JO-3, PO-1, PO-3, LO-1, LO-3, YO-1, YO-3, propidium and psoralen. The integer r is 1-6; the integer t is 1-6; and the integer n is 0-20; Z is a member selected from the group of O, S, $CR^1R^2$, $NR^3R^4$, and $P(O)_2$; $R^1$, $R^2$, $R^3$, and $R^4$ are each members independently selected from the group of H and optionally substituted alkyl.

L is a direct link, or a covalent linkage, wherein the covalent linkage is linear or branched, cyclic or heterocyclic, saturated or unsaturated, having 1-100 atoms selected from the group consisting of C, N, P, O, and S, wherein L can have additional hydrogen atoms to fill valences, and wherein said linkage contains any combination of ether, thioether, amine, ester, carbamate, urea, thiourea, oxy or amide bonds; or single, double, triple or aromatic carbon-carbon bonds; or phosphorus-oxygen, phosphorus-sulfur, nitrogen-nitrogen, nitrogen-oxygen, or nitrogen-platinum bonds; or aromatic or heteroaromatic bonds. R is biomolecule.

In another aspect, the present invention provides a method for detecting incorporation of at least one nucleotide phosphate into a single primer nucleic acid molecule, the method comprising:

i. immobilizing onto a support a polymerase nucleic acid complex comprising a target nucleic acid, a primer nucleic acid which complements a region of the target nucleic acid, and at least one nucleic acid polymerase;

ii. contacting the immobilized complex with at least one type of labeled nucleotide phosphate of Formula II:

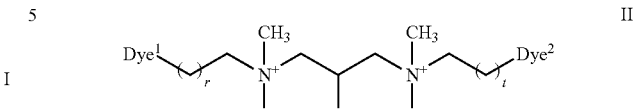

wherein: $Dye^1$ is selected from the group consisting of TO-1, TO-3, BO-1, BO-3, YO-1, YO-3, JO-1, JO-3, PO-1, PO-3, LO-1, LO-3, YO-1, YO-3, propidium and psoralen. $Dye^2$ is selected from the group consisting of TO-1, TO-3, BO-1, BO-3, YO-1, YO-3, JO-1, JO-3, PO-1, PO-3, LO-1, LO-3, YO-1, YO-3, propidium and psoralen. r is 1-6; t is 1-6; n is 0-20; Z is a member selected from the group of O, S, $CR^1R^2$, $NR^3R^4$, and $P(O)_2$; $R^1$, $R^2$, $R^3$, and $R^4$ are each members independently selected from the group consisting of H and optionally substituted alkyl;

L is a direct link, or a covalent linkage, wherein the covalent linkage is linear or branched, cyclic or heterocyclic, saturated or unsaturated, having 1-100 atoms selected from the group consisting of C, N, P, O, and S, wherein L can have additional hydrogen atoms to fill valences, and wherein said linkage contains any combination of ether, thioether, amine, ester, carbamate, urea, thiourea, oxy or amide bonds; or single, double, triple or aromatic carbon-carbon bonds; or phosphorus-oxygen, phosphorus-sulfur, nitrogen-nitrogen, nitrogen-oxygen, or nitrogen-platinum bonds; or aromatic or heteroaromatic bonds. R is biomolecule.

NP is a nucleotide phosphate [NP]; and iii. detecting the incorporation of said at least one type of labeled NP into a single molecule of said primer, while said at least one type of labeled NP is in contact with said immobilized complex, by detecting the label of the NP while said at least one type of labeled NP is in contact with said polymerase nucleic acid complex.

In one embodiment, the polymerase nucleic acid complex is contacted with a single type of labeled NP. In another embodiment, the polymerase nucleic acid complex is contacted with at least two different types of NPs, and wherein each type of NP is uniquely labeled. In yet another embodiment, the polymerase nucleic acid complex is contacted with at least four different types of NPs, and wherein each type of NP is uniquely labeled. In a further embodiment, the NPs are labeled on the γ-phosphate. In certain instances, the NPs are labeled on the γ-phosphate with a fluorescent label.

In another embodiment, detecting the incorporation of the at least one type of labeled NP into a single molecule of the primer comprises detecting a unique signal from the labeled NP using a system or device selected from the group of an optical reader, a high-efficiency photon detection system, a photodiode, a camera, a charge couple device, an intensified charge couple device, a near-field scanning microscope, a far-field confocal microscope, a microscope that detects wide-field epi-illumination, evanescent wave excitation and a total internal reflection fluorescence microscope. In yet another embodiment, the label of the NP is detected using a method comprising a four color evanescent wave excitation device. In a further embodiment, detecting the incorporation of the at least one type of labeled NP into a single molecule of the primer is carried out by a mechanism selected from the group of fluorescence resonance energy transfer, an electron transfer mechanism, a magnetic mechanism, a magneto-resistive mechanism, an excited-state lifetime mechanism and a ground-state complex quenching mechanism.

In yet another embodiment, detecting the incorporation of the at least one type of labeled NP into a single molecule of the primer comprises measuring a residence time of a labeled NP in the polymerase nucleic acid complex. In certain instances, the residence time of an NP that is incorporated into the primer nucleic acid is at least about 100 times longer to about 10,000 times longer than the residence time of an NP that is not incorporated. In certain other instances, the residence time of an NP that is incorporated into the primer nucleic acid is at least about 200 times longer to about 500 times longer than the residence time of an NP that is not incorporated. In yet certain other instances, the residence time of an NP that is incorporated into the primer nucleic acid is about 1.0 milliseconds to about 100 milliseconds. In further instances, the residence time of an NP that is incorporated into the primer nucleic acid is about 2.0 milliseconds to about 10.0 milliseconds.

In another embodiment, the method of the present invention further comprises the step of genotyping the target nucleic acid by determining the identity of at least one NP that is incorporated into a single molecule of the primer. In yet another embodiment, the method of the present invention further comprises sequencing the target nucleic acid by determining the identity and sequence of incorporation of NPs that are incorporated into a single molecule of the primer.

In a further embodiment, the detection is a sequential detection of the identities of more than one uniquely labeled dNPs that are sequentially incorporated into the primer, wherein the sequential detection yields the sequence of region of the target DNA that is downstream of the elongating end of the primer. In another embodiment, the polymerase-nucleic acid complex comprises a target nucleic acid and a nucleic acid polymerase, wherein the polymerase has an attachment complex comprising at least one anchor, which irreversibly associates the target nucleic acid with the polymerase for increasing the processivity index.

These and other objects and advantages will become more apparent when read with the accompanying detailed description and drawings that follow.

DESCRIPTION OF THE DRAWINGS

FIG. 4 illustrates a DNA nanoparticle (SEQ ID NOS:1-11) that a compound of formula I can intercalate.

FIG. 8 illustrates a nucleic acid sample preparation of the present invention.

FIG. 11 illustrates a single molecule isolation embodiment of the present invention.

DETAILED DESCRIPTION OF THE INVENTION

Figure 1:
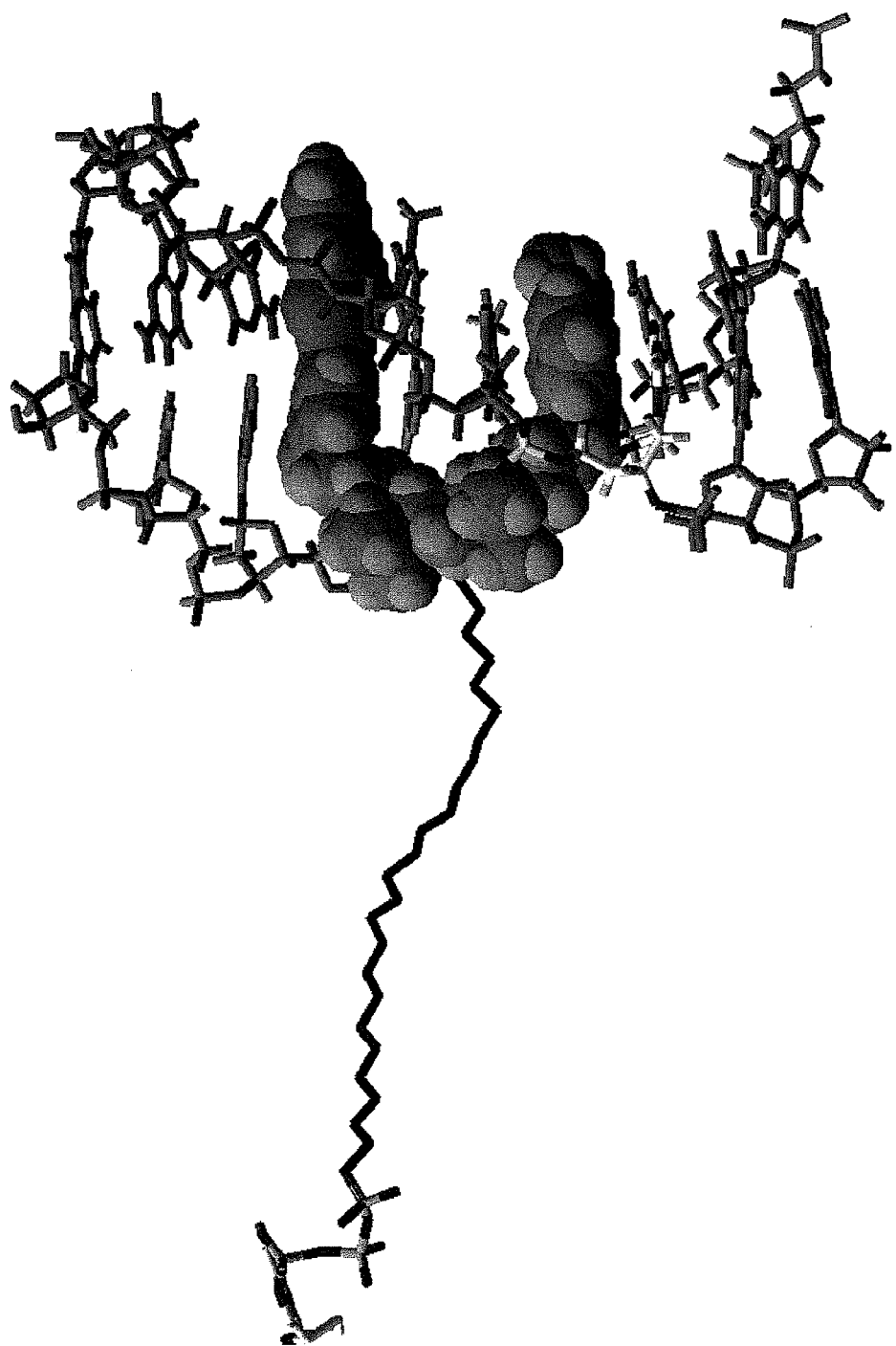
FIG. 1 illustrates a compound of formula I intercalated in DNA.

I. Nucleic Acid Intercalating Agents and Complexes

The present invention provides nucleic acid intercalating agents such as dimeric cyanine dyes (e.g., homodimeric, heterodimeric, trimeric and the like) in the field of structural DNA nanotechnology. As used herein, an intercalating agent or dye is preferably an agent or moiety capable of non-covalent insertion between stacked base pairs in a nucleic acid double helix. Intercalating agents, such as ethidium bromide, fluoresce more intensely when intercalated into double-stranded DNA than when bound to single-stranded DNA, RNA, or in solution. Other intercalating agents exhibit a change in the fluorescence spectra when bound to double-stranded DNA. For example, actinomycin D fluoresces red when bound to single-stranded nucleic acids, and green when bound to a double-stranded template. In certain instances, the intercalating dyes of the present invention provide a detectable signal that is distinguishable when the agent is bound to nucleic acid, or in an unbound state.

In certain aspects, the intercalating dyes of the present invention can be used in detection assays wherein for example, amplification products are detected. In certain aspects, the fluorescence of the inserted dye is detectably distinct from the fluorescence of unbound dye. As such, the compounds, compositions and methods of the present invention can be used for detection and quantification of amplification products, in analytical assays, biological assays and analyte detection assays.

As such, the present invention provides a compound having Formula I:

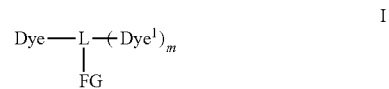

wherein: Dye is a monomeric or dimeric dye (e.g., dimeric TOTO derivative); $Dye^1$ is a monomeric dye; L is a covalent linkage; m is an integer from 0 to 4; and FG is a functional group selected from a reactive group, an activatable group, and a bio-moiety comprising a biomolecule.

In Formula I, L is a covalent linkage or bridge. In certain aspects, for example wherein m is 0, the functional group (FG) is attached to the Dye through a covalent linkage. In other aspects, the covalent linkage L is a bridge connecting Dye, Dye¹ and FG.

L is typically a combination of atoms having stable chemical bonds. L optionally includes single, double, triple or aromatic carbon-carbon bonds, as well as carbon-nitrogen bonds, nitrogen-nitrogen bonds, carbon-oxygen bonds and carbon-sulfur bonds. L typically includes ether, thioether, carboxamide, sulfonamide, urea, urethane or hydrazine moieties. Preferably, L has 1-20 nonhydrogen atoms selected from the group consisting of C, N, O and S; and are composed of any combination of ether, thioether, amine, ester, carboxamide, sulfonamide, hydrazide bonds and aromatic or heteroaromatic bonds. Preferably, L is a combination of single carbon-carbon bonds and carboxamide or thioether bonds. Examples of L include substituted or unsubstituted polymethylene, arylene, alkylarylene or arylenealkyl.

In a preferred embodiment, L is an aliphatic chain containing a backbone of 4-19 carbon atoms. The carbon backbone may be interspersed at one or more intervals with a non-carbon heteroatom. The heteroatoms, which may be the same or different are N, O, or S, preferably N. Where the heteroatom is nitrogen, it is optionally substituted with one or more alkyl substituents having 1-6 carbon atoms, which may be the same or different. In certain aspects, L incorporates quaternary nitrogens, which confer cationic charges on the dimers of the invention, potentially increasing their affinity for nucleic acids, as well as decreasing their ability to permeate cell membranes. In certain aspects, wherein the compound of Formula I incorporates two cyanine subunits, L is independently bound to each subunit.

In certain aspects, the compounds of Formula I have FG attached directly to the Dye. For example, a reactive group is incorporated into at least one of the monomeric dyes of Table I, then bridging linkages can be used between the dyes. For example replacing methyl tosylate in Example 13c with 6-bromohexanoic acid can produce a quaternary salt of the following structure:

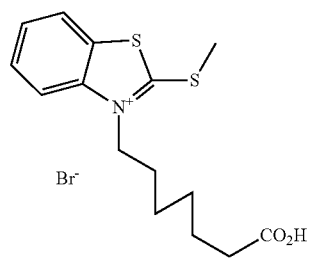

This structure can then be used to make symmetric, dimeric dyes with an activatable carboxylic acid group on each monomeric dye or asymmetric dyes with a single such group:

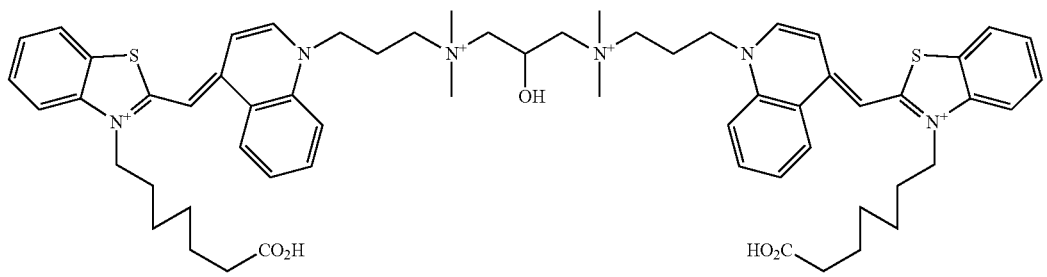

Activation of these carboxylic acids to NHS esters for example, produces a reactive intercalating dye. This dye can be used to label, for example, an antibody, such as a secondary, goat-anti-mouse antibody. Treatment of the antibody with a plasmid DNA double helix, for example, leads to a highly fluorescent immunochemical probe for mouse antibodies.

In certain preferred aspects, the compounds of Formula I have Formula Ia:

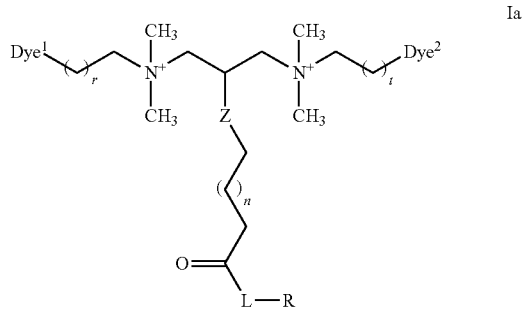

wherein Dye¹, Dye² Z, r, t, n, L and R have been defined above. In certain preferred aspects, Dye¹ and Dye² are independently selected from BO-1, BO-3, JO-1, LO-1, PO-1, PO-3, TO-1, TO-3, YO-1, YO-3; and psoralen. Those of skill in the art will know of other dyes suitable for use in the present invention.

R is selected from the group of a small molecule, a marker, a cell, a liposome, a protein, a peptide, an enzyme substrate, a hormone, an antibody, an antigen, a hapten, an avidin, a streptavidin, biotin, a carbohydrate, an oligosaccharide, a polysaccharide, a nucleic acid, a deoxy nucleic acid, a fragment of DNA, a fragment of RNA, nucleotide phosphate, acyclo terminator triphosphates, dideoxy terminator triphosphates, and PNA. Preferably, R is a nucleotide phosphate (NP).

In Formula Ia, L is preferably of the formula:

$$-R^1-X^1-Y^1-$$

wherein:
$R^1$ is an O, S or optionally substituted nitrogen and a direct link; $X^1$ is a direct link and $C_2$-$C_{50}$ alkylene optionally interrupted by a heteroatom; and $Y^1$ is a direct link, oxygen, an optionally substituted nitrogen and sulfur.

In a preferred embodiment, $Dye^1$ is the same as $Dye^2$. In certain preferred aspects, the biomolecule is a nucleotide phosphate such as a nucleotide monophosphate, di-, tri-, tetra, penta-, or hexaphosphate, preferably, the biomolecule is a nucleotide triphosphate.

In other preferred embodiments, r is 1, 2, 3, 4, 5 or 6; t is 1, 2, 3, 4, 5 or 6; n is 4, 5, 5, 6, 7, 8, 9, 10, 11, or 12. In other aspects, $R^1$ is nitrogen; $X^1$ is $(OCH_2CH_2)_{1-25}$; and $Y^1$ is nitrogen.

In certain aspects, the compound of Formula I has Formula II:

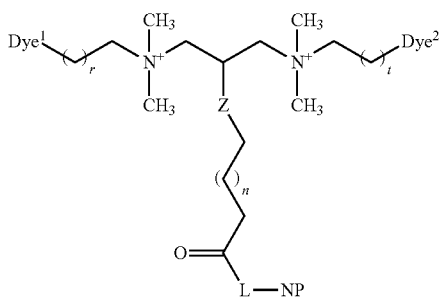

wherein NP is a nucleotide phosphate (NP). Certain compounds of Formula II are preferred. Such compounds include:

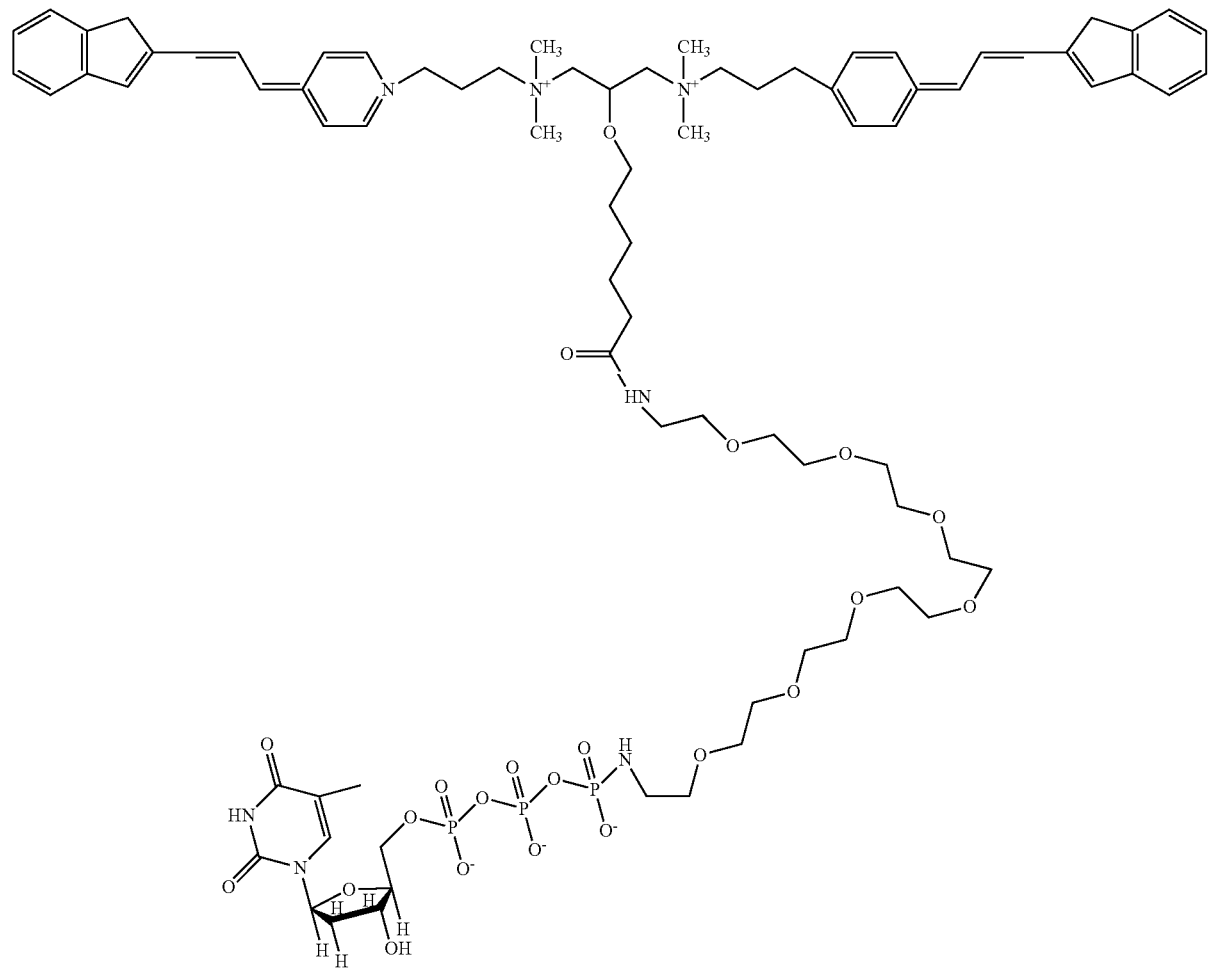

or;

-continued

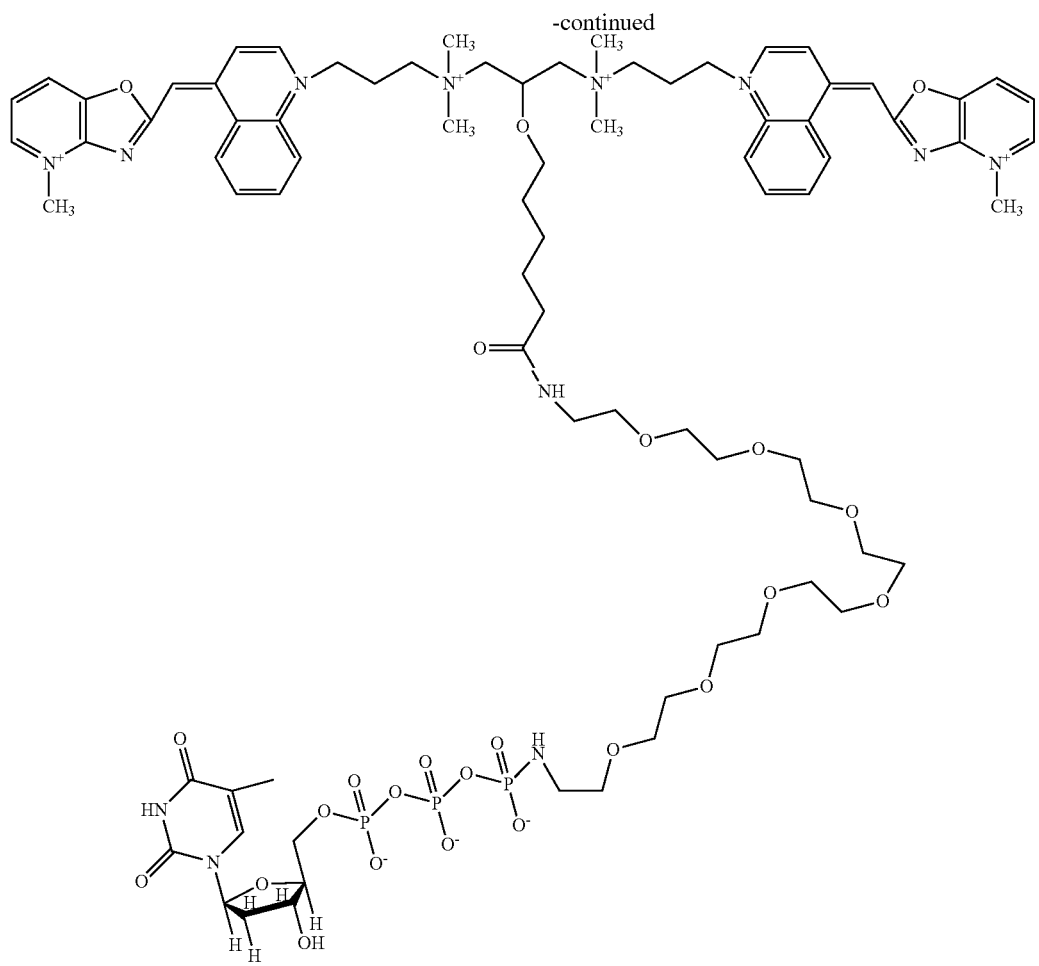

A wide variety of dyes such as cyanine dyes, are suitable for the present invention. In certain aspect, the cyanine based chromophores, have absorption and emission maxima ranging from 500 nm to 750 nm or higher, and can be readily synthesized by linking the appropriate quaternized, heteroaromatic nuclei through a methine (polymethine) bridge (see below). Table I sets forth certain preferred Dye[1] and Dye[2] structural units suitable for use in the present invention.

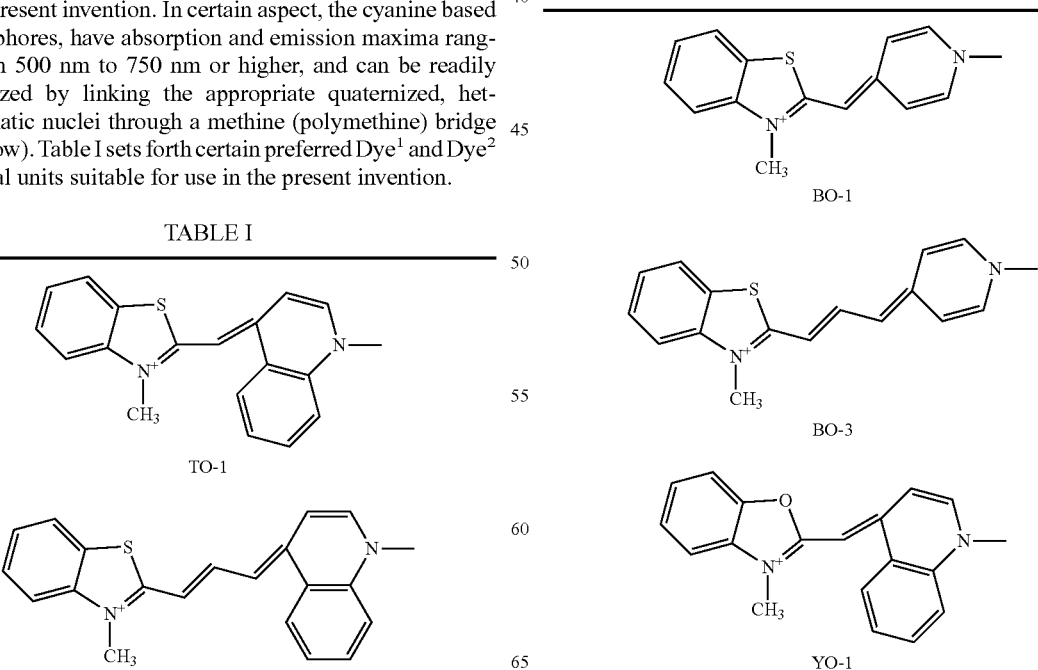

TABLE I-continued

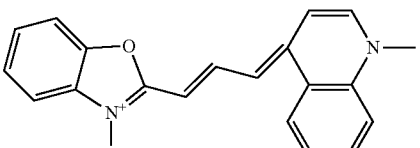
YO-3

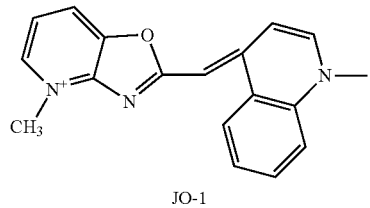
JO-1

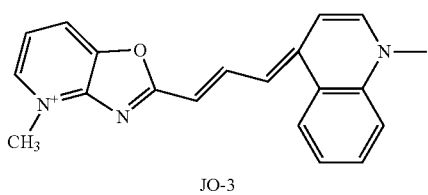
JO-3

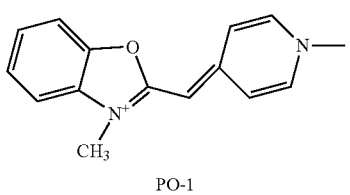
PO-1

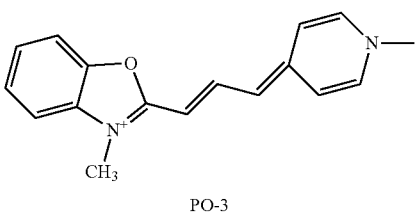
PO-3

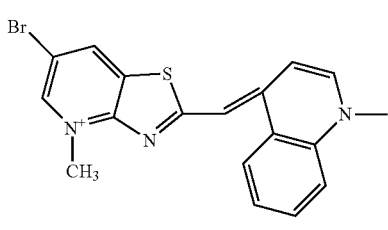
LO-1

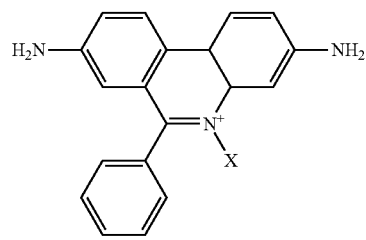
propidium and ethidium "monomer"

TABLE I-continued

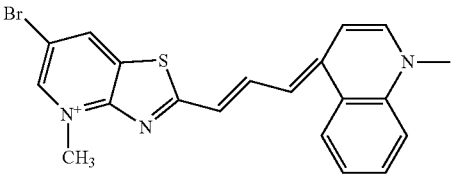
LO-3

In certain preferred aspects, the asymmetric cyanine dyes TO-1, YO-1 and JO-1 are preferred. For example, the monomeric dyes, TO and YO, have large extinction coefficients (e>70,000M-1 cm-1), while those of the dimeric dyes, TOTO and YOYO, exceed 100,000 M-1 cm-1. In aqueous solution, all four dyes are virtually non-fluorescent. Complex formation with dsDNA results in a very large increase in the fluorescence quantum yield. Other dyes suitable for use in the present invention are disclosed in U.S. Pat. Nos. 6,664,047; 5,582,997; 5,410,030; 5,863,753; 5,321,130; 5,656,449; 5,658,751; 5,436,134; 5,597,696, all of which are incorporated herein by reference.

In another aspect, nucleotide triphosphates are linked through their terminal phosphate group (γ-phosphate) to a bridge moiety on a intercalating dye of the present invention. In a preferred aspect, the strong complex formed between these dyes and double-stranded DNA allows facile attachment of biomolecules (e.g., dNTPs or other moieties) to DNA at labeling ratios defined by the dye:basepair stoichiometry in the staining solution.

As shown in FIG. 1, once these compounds of formula I are intercalated into DNA, these "nanoparticles" are of defined molecular structure, with strong fluorescence emission, strong anionic charge, excellent colloidal stability, and a high surface density of phosphate-linked nucleotide triphosphates as a substrate for DNA polymerases. As such, these nanoparticles use DNA as a construction material. The extraordinarily tight complex between dimeric cyanine dyes and DNA provide new opportunities in structural DNA nanotechnology.

Figure 2:
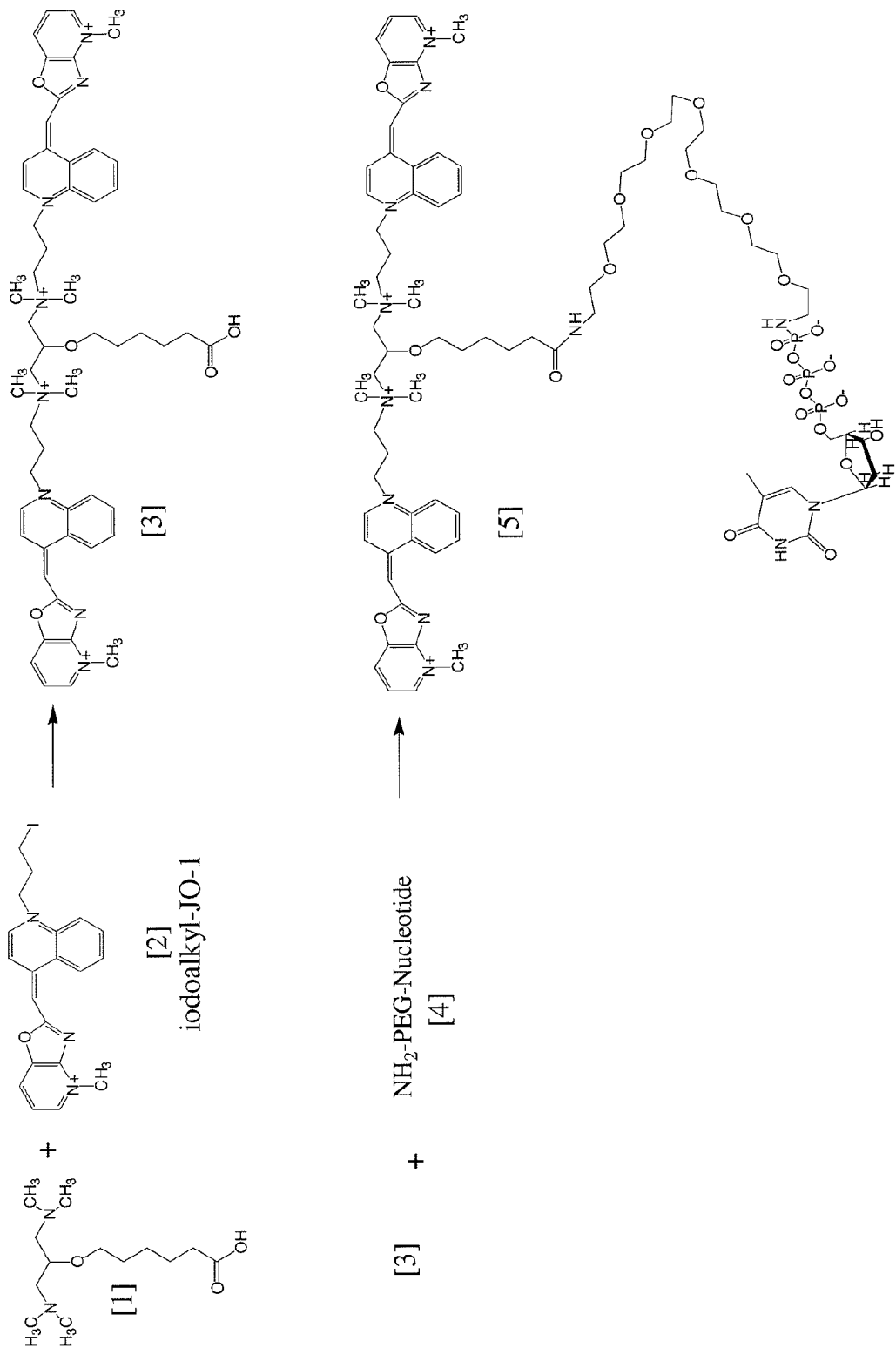
FIG. 2 illustrates a synthetic scheme for a compound of the present invention.
Figure 3:
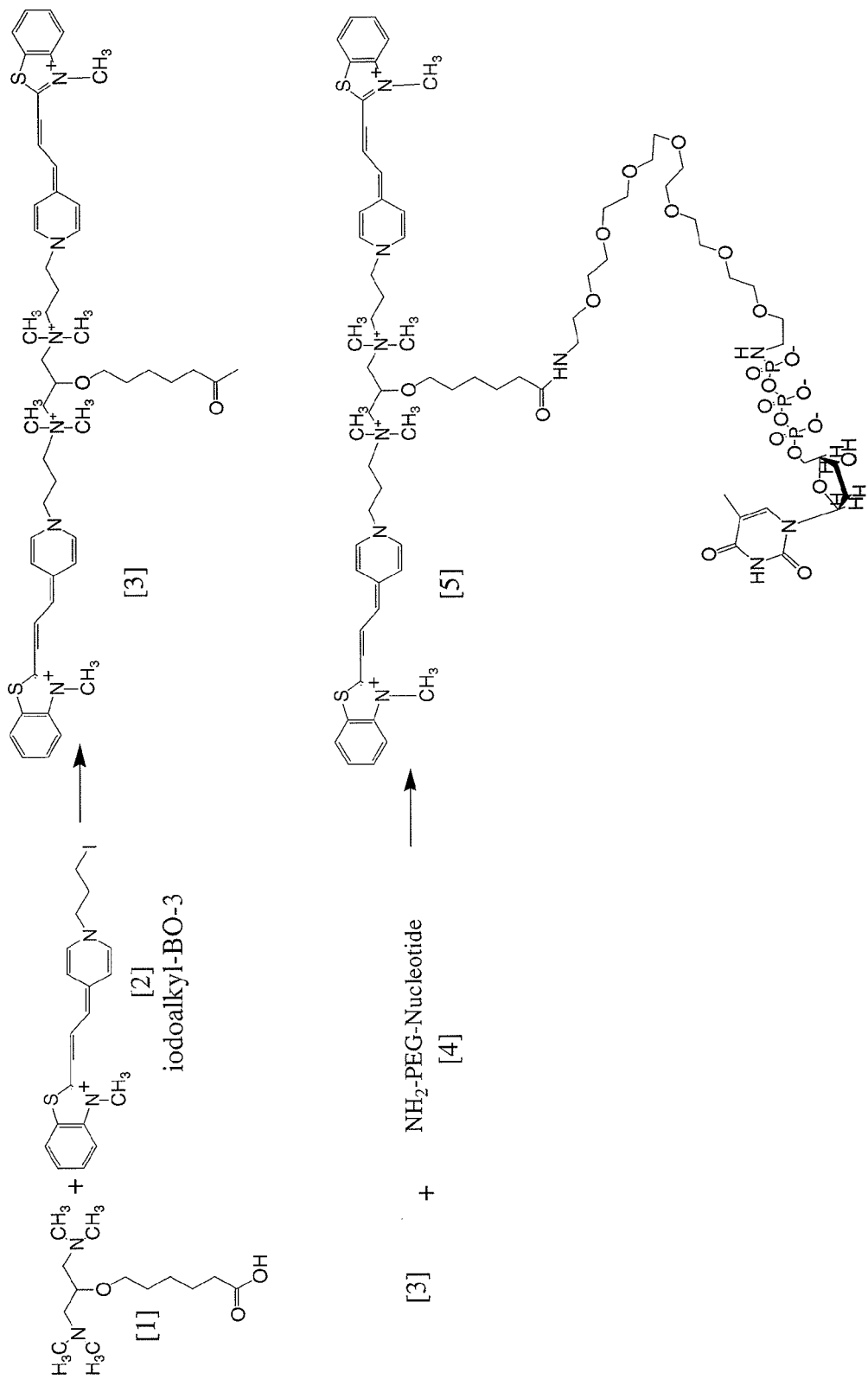
FIG. 3 illustrates a synthetic scheme for a compound of the present invention.

With reference to FIG. 2, in one embodiment, the compounds of formula I can be synthesized using the illustrated method. The bridge compound 1 is reacted with the iodoalkyl forms of a monomeric dye 2 such as for example, JO-1 (FIG. 2) or BO-3 (FIG. 3) to generate a dimeric dye 3. Other monomers like BO-1, BO-3, JO-1, LO-1, PO-1, PO-3, TO-1, TO-3, YO-1, YO-3 or psoralen are also suitable as iodoalkyl dye derivatives. Thereafter, dimeric dye 3 is reacted with an amino-PEG-biomolecule, such as an amino-PEG-nucleotide. This reaction generates compound 5. In addition, dyes of the present invention are not limited to dimers like JOJO or BOBO as shown in FIG. 2 and FIG. 3, but also include trimers such as JOJOJO or tetramers like BOBOBOBO. Multimeric dyes (containing greater than two monomer dyes) in some instances will bind tighter to DNA than the corresponding monomers or dimers. In FIG. 2 and FIG. 3, the D-2-deoxyribose is preferred.

Advantageously, compounds such as 1,1'-(4,4,7,7-tetramethyl-4,7-diazaundecamethylene)-bis-4-[3-methyl-2,3-dihydro-(benzo-1,3-thiazole)-2-methylidene]-quinolinium tetraiodide (TOTO) and its benzoxazole analogue, 1,1'-(4,4,7,7-tetramethyl4,7-diazaundecamethylene)-bis4-[3-methyl-2,3-dihydro-(benzo-1,3-oxazole)-2-methylidene]-quinolinium tetraiodide) (YOYO) form stable highly fluorescent complexes with dsDNA with fluorescence enhancements greater than a 1,000-fold. These dyes allow much more sensitive fluorescence detection of dsDNA (see, Rye et al., *Nucleic Acid Research*, Vol. 20, 2803-2812 (1992), incorporated herein by reference), but also it is possible to use the highly fluorescent complexes with dsDNA as substrates for polymerases in the methods of the present invention.

The present invention also provides compositions or complexes, wherein at least two compounds of Formula I (such as at least two compounds of Formula II) are intercalated into a single DNA molecule. For example, several molecules of the same type of labeled NP (e.g. dATP-JOJO-1) are intercalated either into a single DNA molecule or into a complex of DNA molecules to form an intercalation complex. In a given intercalation complex, all of the NPs can be labeled with the same label (e.g. JOJO-1). Alternatively, different labels may be attached to the same type of NP so that the intercalation complex contains a mixture of labels, but having just one type of NP (e.g. dGTP-JOJO-1 plus dGTP-BOBO-3). This allows 2 or more unique labels to be used in unique mixtures in order to provide 4 unique spectral patterns to intercalation complexes. For example, a set of 4 intercalation complexes could comprise: Complex 1 containing 100% dATP-JOJO-1; Complex 2 containing 100% dCTP-BOBO-3; Complex 3 containing 33% dGTP-JOJO-1 plus 67% dGTP-BOBO-3; and Complex 4 containing 75% dTTP-JOJO-1 plus 25% dTTP-BOBO-3. In this example, only two labels are used, BOBO-3 and JOJO-1, but four complexes are generated giving rise to unique fluorescence spectra. Thus, each complex contains a unique NP type, but each NP type is individually labeled with either JOJO-1 or BOBO-3. In a further embodiment, the label may contain more than two dyes, wherein all of the dyes comprises a single label using either the same dye (e.g. thiazole orange) or different dyes (e.g. thiazole orange, oxazole yellow, JO-1).

In other embodiments, the present invention provides a intercalating complex (Ic) comprising a nucleic acid and a intercalating dye. The nucleic acid can be for example, DNA, RNA, PNA, or combinations thereof, and the Ic has at least one dye such as an intercalating dye. In certain instances, the nucleic acid is a plasmid or circular DNA with at least one intercalating dye. In other instances, the nucleic acid has multiple dyes associated therewith. The composition preferably has covalently attached thereto a member of a binding pair and therefore can be used as a fluorescent probe. As such, the present invention provides a fluorescent probe having Formula III:

wherein: Ic is an intercalated complex, wherein the intercalated complex (Ic) comprises a least one intercalating dye and a nucleic acid; BM is a member of a specific binding pair; L is a linkage between the intercalated complex and BM. The BM is a specific binding pair member such as for example, a protein, an amino acid, an immune stimulator, an avidin, a drug, a hapten, an enzyme, an enzyme substrate, a primary or secondary antibody, a biotin, a nucleic acid, a polysaccharide, a liposome, a lipid, a carrier compound, a bioaffinity compound, an analytically detectable compound and a therapeutically active compound.

In certain aspects, the present invention provides methods of using the fluorescent probes by combining a compound of Formula III with a sample that contains, or is thought to contain the desired analyte, incubating the mixture of dye and sample for a time sufficient for the dye to combine with the analyte in the sample to form one or more dye-analyte complexes having a detectable fluorescent signal. The characteristics of the dye-analyte complex, including the presence, location, intensity, excitation and emission spectra, fluorescence polarization, fluorescence lifetime, photobleaching rate and other physical properties of the fluorescent signal can be used to detect, differentiate, sort, quantitate, and/or analyze aspects or portions of the sample. The dyes of the invention are optionally used in conjunction with one or more additional reagents (preferably detectably different fluorescent reagents), including dyes of the same class having different spectral properties.

In one embodiment of the invention, the analyte is a nucleic acid polymer, such as DNA or RNA. In another embodiment of the invention, the analyte is a lipid-complexed poly(amino acid). By poly(amino acid) is meant any polymer of amino acid subunits, artificial or natural, such as peptides and proteins, and including glycoproteins, lipoproteins and other modified proteins.

In one example, "Ic" is a plasmid/dye intercalation complex; "L" is the 5 methylene groups leading from dye to an antibody such as a secondary, goat-anti-mouse antibody; and "BM" is the antibody (and the carbonyl group of the former NHS ester/carboxylic acid in the activated 6-bromohexanoic acid compound described above.

Turning to FIG. 4, illustrated therein is a DNA nanoparticle constructed of eight complementary 170-mer oligonucleotides (Ring 1-8), one 81-mer, one 41-mer (Start B) and one 40-mer (Start A). The underlined nucleotide letters are the 5'-end of each oligo; so each "Ring" type sequence should be read from the 5'-end continuously around the circle to the 3'-end. Dash and plus characters indicate base pairing between complementary strands.

Brackets represent four T's (dTp)4 connecting contiguous sequences spanning two lines. Dots in the sequence strings represent placeholders to better align the displayed sequences (i.e. dots are not a nucleotide, not a strand break). Gaps (vertically aligned with the dots) represent strand breaks between the 5'- and 3'-ends of juxtaposed oligos. It is believed these physical breaks will promote more efficient staining with the dyes of the present invention, by allowing for topological relaxation.

Figure 5:
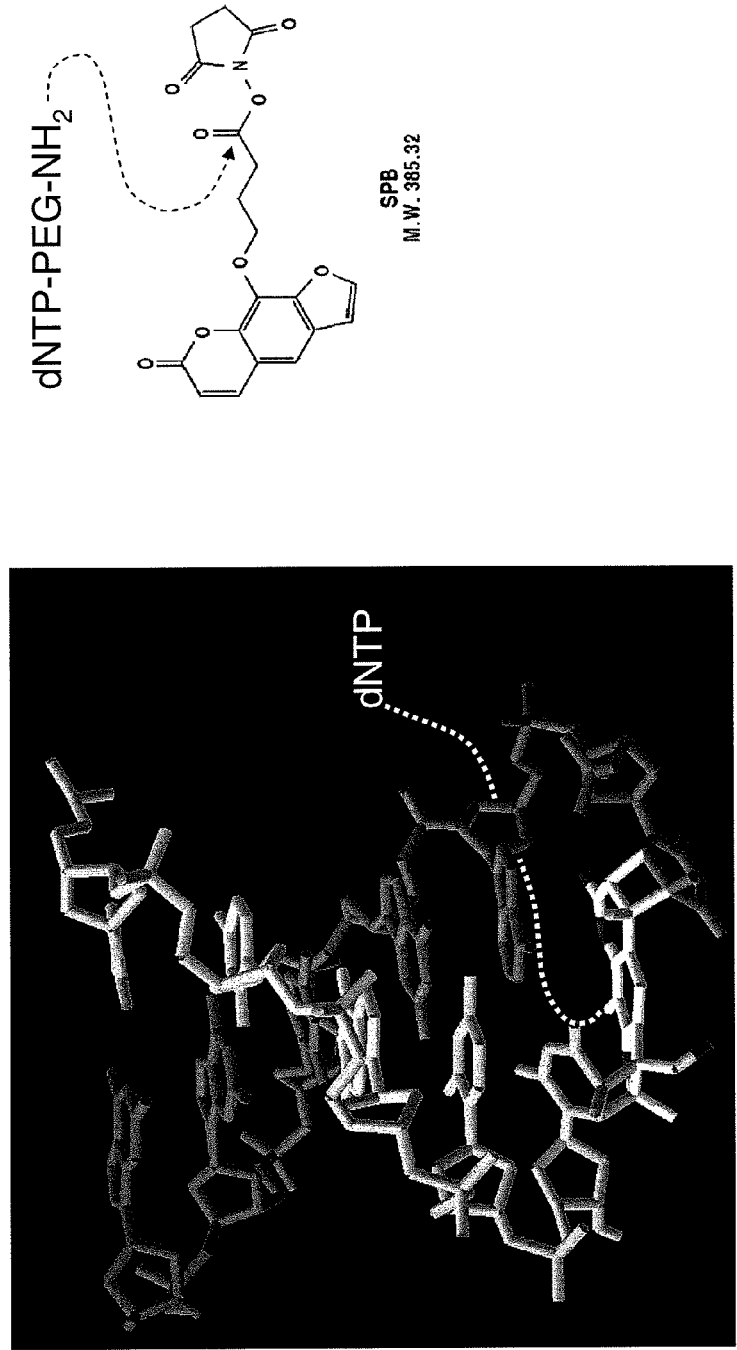
FIG. 5 illustrates a nucleotide-psoralen conjugate intercalated in a DNA strand.

As shown in FIG. 5, compounds of Formula II, can intercalate into DNA strands. In turn, these interacted compounds of Formula II can be used as substrates in the methods of the present invention. In one preferred aspect, a nanoparticle particle comprising 1,520 nucleotide bases and about 70 dimeric cyanine intercalating dyes can be made and used in sequencing methods of the present invention. Preferred dyes are JOJO-1 and BOBO-3 because both can be excited by a single laser line (532 nm), thus simplifying the construction and minimizing the cost of a commercial sequencing instrument. Individual DNA molecules are stained with mixtures of JOJO-1 and BOBO-3, and 4 different dye mixtures that can be reliably distinguished from the signal ratio between 2 emission channels. In this example, detection is by CCD camera, signal-to-noise is high, and photobleaching is insignificant at the short exposure times employed in this system. Nucleic acid sequencing using single molecule detection is preferred.

II. Polymerase-Nucleic Acid Complex

In one embodiment, the present invention provides a polymerase-nucleic acid complex (PNAC), comprising: a target nucleic acid and a nucleic acid polymerase, wherein the polymerase has an attachment complex comprising at least one anchor, which at least one anchor irreversibly associates the target nucleic acid with the polymerase to increase the processivity index. As used herein, the term "processivity index" means the number of nucleotides incorporated before the polymerase dissociates from the DNA. Processivity refers to the ability of the enzyme to catalyze many different reactions without releasing its substrate. That is, the number of phosphodiester bonds formed using the present invention is greatly increased as the substrate is associated with polymerase via an anchor.

In one embodiment, the processivity index is defined as the number of nucleotides sequenced divided by the number of nucleotides in the template. For example, if the template is 10,000 bases long, and the PNAC sequences 9000 bases, the index is 0.90. Using the PNACs and methods of the present invention, the index is preferably between at least 0.5 to about 1. More preferably, the index is about at least 0.80 to about 1, such as at least 0.80, or at least 0.85, or at least 0.90, or at least 0.95, or 1.0.

Using the PNACs of the present invention, because the target is irreversibly associated with the polymerase, the number of nucleotides added can be from about 20 to about 100,000, such as about 1000 to about 30,000, such as about 5000 to about 20,000.

Figure 6:
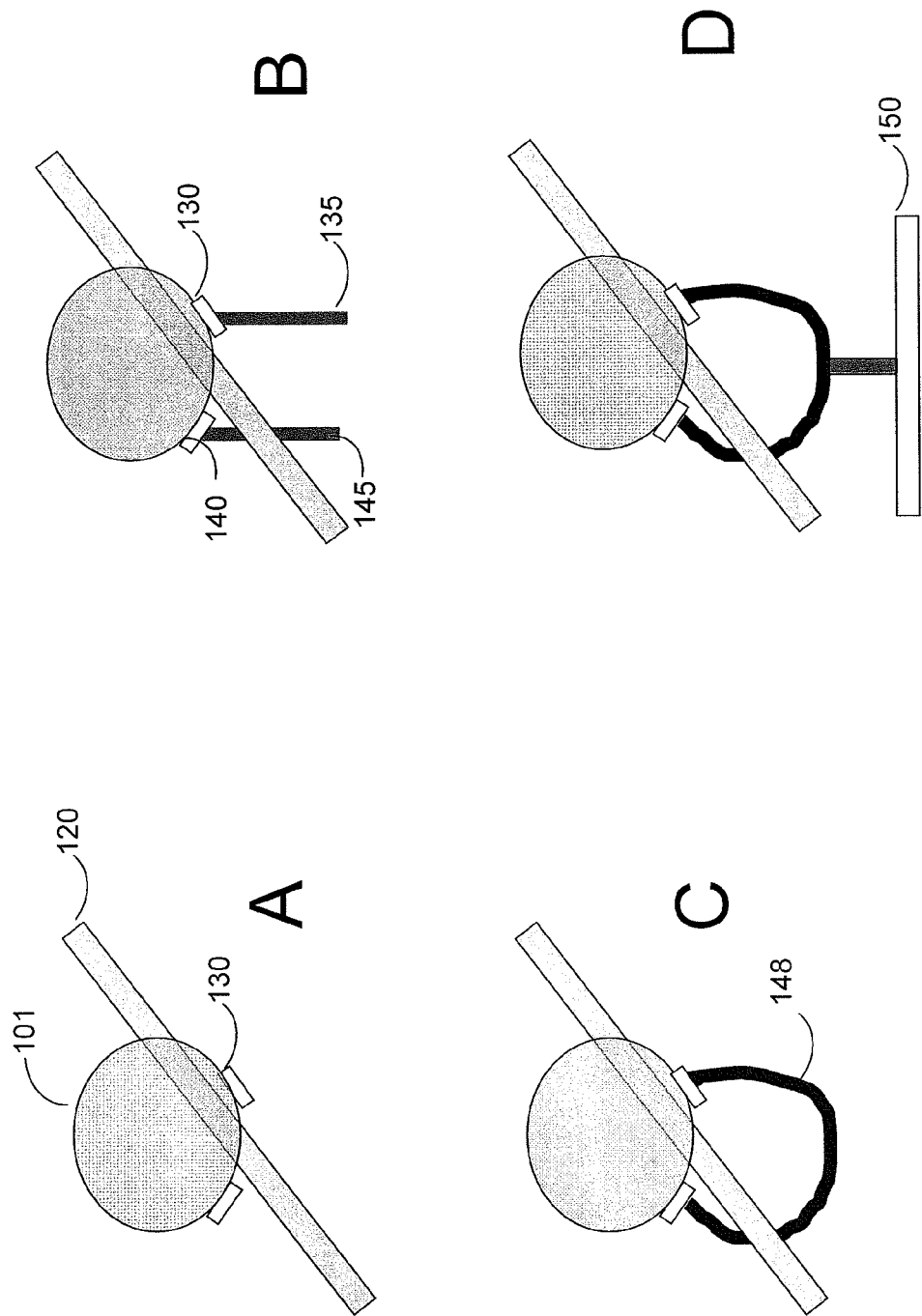
FIG. 6 illustrates various features of a polymerase-nucleic acid complex of the present invention.

FIG. 6 A-D are examples of polymerase nucleic acid complexes (PNACs) of the present invention. This diagram is merely an illustration and should not limit the scope of the claims herein. One of ordinary skill in the art will recognize other variations, modifications, and alternatives.

The polymerase-nucleic complex comprises at least one anchor. In certain aspects, the PNAC will further comprise a primer, which complements a region of the target nucleic acid. As shown in FIG. 6A, the polymerase 101 can have at least one anchor 130 such anchor comprising for example, an amino acid, an epitope, a modified amino acid and the like, for attaching a topological tether. The amino acid i.e., anchor can be for example, a cysteine or a histidine. In certain aspects, the polymerase nucleic acid complex, wherein the nucleic acid 120 is preferably within the active site, comprises at least two anchors. Suitable anchors of the present invention include, but are not limited to, an amino acid, a modified amino acid, a peptide, a histidine tag, a histidine patch, an eptiope, and the like. In certain instances, the at least one anchor entraps the target nucleic acid such as by folding back on itself. In other instances, the anchors of the present invention are useful for also attaching a topological tether to the polymerase, or for example, attaching the PNAC to a substrate. In other embodiments, the anchor affixes the PNAC to a support, with or without a topological tether. In certain other embodiments, the polymerase-nucleic complex comprises a topological tether bound to at least two anchors.

As shown in FIG. 6B, an anchor 130 can further comprise other functionalities such as a first member 135 of a first binding pair. A second anchor 140 has a first member 145 of a second binding pair. As shown in FIG. 6C, in certain instances, a topological tether is formed when the first members 135, 145 are joined by a common member 148. Alternatively, a topological tether can be formed when the first members 135, 145 are each joined directly to a support (not shown). A topological tether and at least one anchor can attach via complementary binding pairs. Alternatively, the anchors can attach directly to a substrate without the use of a tether (for example, histidine patches as anchors bound directed to a Ni surface). Suitable complementary binding pairs include, but are not limited to, any haptenic or antigenic compound in combination with a corresponding antibody or binding portion or fragment thereof, nonimmunological binding pairs, receptor-receptor agonist or antagonist, IgG-protein A, lectin-carbohydrate, enzyme-enzyme cofactor, enzyme-enzyme-inhibitor, and complementary polynucleotide pairs capable of forming nucleic acid duplexes.

Exemplary complementary binding pairs include, but are not limited to, digoxigenin and anti-digoxigenin, fluorescein and anti-fluorescein, dinitrophenol and anti-dinitrophenol, bromodeoxyuridine and anti-bromodeoxyuridine, mouse immunoglobulin and goat anti-mouse immunoglobulin, biotin-avidin, biotin-streptavidin, thyroxine and cortisol, histidine patch and Ni-NTA and acetylcholine and receptor-acetylcholine. In certain aspects, the anchor comprises at least one amino acid or an epitope for attaching the topological tether.

As discussed, in certain instances, anchors can comprise an amino acids capable of modification for attachment to a binding member, a tether, a support, and combinations thereof. In one embodiment, a topological tether can attach to two anchors, without intervening binding pairs.

In one aspect, the anchor comprises a biotin moiety. For example, biotin-X nitrilotriacetic acid can be used to covalently attach the biotin moiety to a protein having a free amino group. In turn, this biotin anchor can attach to a streptavidin or a neutraviden binding member, or alternatively, directly to a streptavidin or a neutravidin support.

In another aspect, the topological tether comprises an antibody. In certain embodiments, the topological tether is an antibody that can attach via anchors having complementary binding pairs. For example, the two anchors can be histidine tags, and the tether can be an antibody. In certain aspects, the polymerase-nucleic complex comprises a topological tether anchored to a solid support 150 (see, FIG. 6D).

In certain aspects, the polymerase-nucleic acid attachment complex can be attached to the substrate by providing an anchor such as a polyhistidine tag, that binds to metal. Other conventional means for attachment employ binding pairs. Alternatively, covalent crosslinking agents can be employed such as reagents capable of forming disulfide (S—S), glycol (—CH(OH)—CH(OH)—), azo (—N=N—), sulfone (—S(=O2-), ester (—C(=O)—O—), or amide (—C(=O)—N—) bridges. The covalent bond is for example, an amide, a secondary or tertiary amine, a carbamate, an ester, an ether, an oxime, a phosphate ester, a sulfonamide, a thioether, a thiourea, or a urea.

Selected examples of reactive functionalities useful for the attaching an anchor to the polymerase, a tether to the anchor, or the PNAC to the substrate are shown in Table II, wherein the bond results from such a reaction. Those of skill in the art will know of other bonds suitable for use in the present invention.

TABLE II

| Reactive functionality (A) | Complementary group (B) | The resulting bond (C) |
| --- | --- | --- |
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |

TABLE II-continued

| Reactive functionality (A) | Complementary group (B) | The resulting bond (C) |
| --- | --- | --- |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides/imides |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols (amines) | thioethers (alkyl amines) |
| epoxides | carboxylic acids | esters |
| haloacetamides | thiols | thioethers |
| haloplatinate | amino | platinum complex |
| haloplatinate | heterocycle | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonyl halides | amines/anilines | sulfonamides |

In certain aspects, the polymerase can be covalently attached to a support (e.g., coverslip, metal surface, and the like), wherein the polymerase is labeled in vivo with a modified amino acid such as for example, a benzaldehyde derivative of phenylalanine. In one example, the benzaldehyde derivative of phenylalanine is p-acetyl-L-phenylalanine, which can be labeled at specific position(s) in the polymerase. This can be accomplished using organisms (e.g., E. coli, yeast) engineered to have an augmented 21-amino acid genetic code capable of inserting p-acetyl-L-phenylalanine at specific codons (see, Lei Wang, Zhiwen Zhang, Ansgar Brock, Peter G. Schultz (2003) Proc Natl Acad Sci USA 100:56-61). In one aspect, the polymerase gene of the present invention is engineered to have the appropriate codon or codons at the desired anchor positions, and the corresponding polymerase protein is expressed in the 21-amino acid organism. The expressed polymerase is then purified, mixed with the template DNA, and the resulting PNACs are contacted to a support derivatized with a hydrazine, hydrazone, and the like (e.g., SANH from Solulink Inc). Alternatively, a chemical functionality equivalent to p-acetyl-L-phenylalanine can be attached to the protein at specific or unspecific positions by conjugating SFB (Solulink Inc) to lysine amino acids on the protein. The functionalized protein is attached to the support as above.

Figure 7:
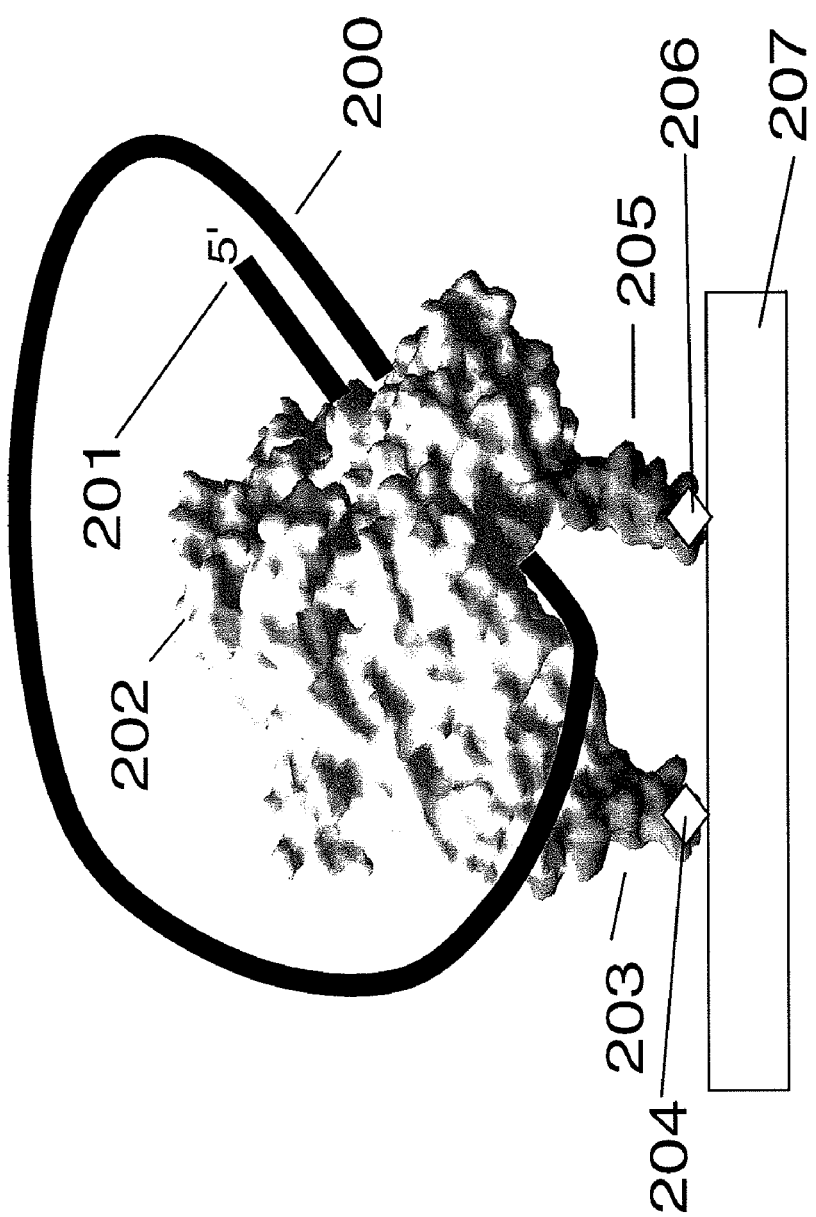
FIG. 7 illustrates an anchor embodiment of the present invention.

FIG. 7 shows a structural model of a PNAC comprising a 9 Degrees North DNA polymerase (parent of Therminator polymerase) 202 and a circular primed DNA template 200. This diagram is merely an illustration and should not limit the scope of the claims herein. One of ordinary skill in the art will recognize other variations, modifications, and alternatives. The polymerase 202 comprises anchors 203 and 205 inserted at Therminator amino acid positions K53 and K229, respectively. The anchors are identical in amino acid sequence (LL-SKKRSLCCXCTVIVYVTDT; SEQ ID NO:16), wherein the anchor comprises amino acid pa-Phe, which is indicated by "X" in the sequence and by white diamonds 204, 206. The pa-Phe amino acids 204, 206 are shown attached to the support 207. The circular DNA template 200 is hybridized to a primer 201. The 5'-end of the primer is indicated 201 and the 3'-end of the primer is hidden in the DNA binding cleft of the protein 202. The structural model is 1QHT.pdb in the protein database at http://www.rcsb.org/pdb/.

As discussed, the Therminator DNA polymerase can be modified by inserting a 20-amino acid anchor at position K53 and a 20-amino acid anchor at position K229 in the Therminator gene. These two positions straddle the DNA binding cleft as shown in FIG. 2. As shown therein, each 20-amino acid anchor is engineered to contain at least one p-acetyl-L-phenylalanine (pa-Phe) amino acid near the middle of the anchor (FIG. 7). The engineered protein is then purified. In one embodiment, to make polymerase nucleic acid complexes, the purified Therminator protein is mixed with a primed single stranded circular DNA template and the mixture is contacted with a support derivatized with hydrazine or hydrazone linkers (Solulink Inc). Optionally, the template DNA contains at least one dUTP base positioned 4-5 bases from the 3'-end of the primer in order to stabilize the polymerase-DNA complex as described (see, Mark Fogg, Laurence Pearl, Bernard Connolly (2002) Nature Structural Biology 9:922-927). The polymerase-DNA complex attaches to the support by bond formation between the pa-Phe on the protein and the hydrazine or hydrazone linker on the support. Optionally, the kinetics of bond formation can be increased by concentrating polymerase-DNA complexes on the support surface using an energy field (e.g., electric field, pressure field, magnetic field, and the like). Once the PNAC has formed on the support, the circular DNA is irreversibly associated with the polymerase as shown in FIG. 7.

A. Polymerases

The polymerases suitable for use in the present invention preferably have a fidelity (incorporation accuracy) of at least 99%. In addition, the processivity of the polymerase should be at least 20 nucleotides, prior to immobilization. Although the polymerase selected for use in this invention is not critical, preferred polymerases are able to tolerate labels on the γ-phosphate of the NP.

In certain aspects, the polymerases useful in the present invention are selected from the A family polymerases or the B family polymerases. DNA-dependent DNA polymerases have been grouped into families, including A, B, X, and others on the basis of sequence similarities. Members of family A, which includes bacterial and bacteriophage polymerases, share significant similarity to E. coli polymerase I; hence family A is also known as the pol I family. The bacterial polymerases also contain an exonuclease activity, which is coded for in the N-terminal portion. Family A polymerases include for example, Klenow, Taq, and T7 polymerases. Family B polymerases include for example, the Therminator polymerase, phi29, RB-69 and T4 polymerases.

In certain instances, suitable DNA polymerases can be modified for use in the present invention. These polymerases include, but are not limited to, DNA polymerases from organisms such as Thermus flavus, Pyrococcus furiosus, Thermotoga neapolitana, Thermococcus litoralis, Sulfolobus solfataricus, Thermatoga maritima, E. coli phage T5, and E. coli phage T4. The DNA polymerases may be thermostable or not thermostable.

In other embodiments, the polymerases include T7 DNA polymerase, T5 DNA polymerase, HIV reverse transcriptase, E. coli DNA pol I, T4 DNA polymerase, T7 RNA polymerase, Taq DNA polymerase and E. coli RNA polymerase. In certain instances, exonuclease-defective versions of these polymerases are preferred. The efficiency with which γ-labeled NPs are incorporated may vary between polymerases; HIV-1 RT and *E. coli* RNA polymerase reportedly readily incorporate γ-labeled nucleotide. The polymerase can also be a T7 polymerase. T7 polymerase has a known 3D structure and is known to be processive. In order to operate in a strand-displacement mode, the polymerase requires a complex of three proteins: T7 polymerase+thioredoxin+primase (Chowdhury et al. *PNAS* 97:12469). In other embodiments, the polymerases can also be HIV RT and DNA Polymerase I.

B. Sources of Target Nucleic Acid.

The identity and source of the template and primer nucleic acid ("NA") is generally not critical, although particular NAs are needed for specific applications. NA used in the present invention can be isolated from natural sources, obtained from such sources such as ATCC, GenBank libraries or commercial vendors, or prepared by synthetic methods. It can be mRNA, ribosomal RNA, genomic DNA or cDNA, an oligonucleotide, which can be either isolated from a natural source or synthesized by known methods. When the target (i.e., template) NA is from a biological source, there are a variety of known procedures for extracting nucleic acid and optionally amplified to a concentration convenient for genotyping or sequence work. Nucleic acid can be obtained from any living cell of a person, animal or plant. Humans, pathogenic microbes and viruses are particularly interesting sources.

Nucleic acid amplification methods are also known and can be used to generate nucleic acid templates for sequencing. Preferably, the amplification is carried out by polymerase chain reaction (PCR) (U.S. Pat. Nos. 4,683,202. 4,683,195 and 4,889,818; Gyllenstein et al., 1988, *Proc. Natl. Acad. Sci. USA* 85: 7652-7656; Ochman et al., 1988, *Genetics* 120: 621-623; Loh et al., 1989, *Science* 243: 217-220; Innis et al., 1990, PCR PROTOCOLS, Academic Press, Inc., San Diego, Calif.). Other amplification methods known in the art can be used, including but not limited to ligase chain reaction, use of Q-beta replicase, or methods listed in Kricka et al., 1995, MOLECULAR PROBING, BLOTTING, AND SEQUENCING, Chap. 1 and Table IX, Academic Press, New York.

Any NA used in the invention can also be synthesized by a variety of solution or solid phase methods. Detailed descriptions of the procedures for solid phase synthesis of nucleic acids by phosphite-triester, phosphotriester, and H-phosphonate chemistries are widely available. See, for example, Itakura, U.S. Pat. No. 4,401,796; Caruthers, et al., U.S. Pat. Nos. 4,458,066 and 4,500,707; Beaucage, et al., Tetrahedron Lett., 22:1859-1862 (1981); Matteucci, et al., J. Am. Chem. Soc., 103:3185-3191 (1981); Caruthers, et al., Genetic Engineering, 4:1-17 (1982); Jones, chapter 2, Atkinson, et al., chapter 3, and Sproat, et al., chapter 4, in *Oligonucleotide Synthesis: A Practical Approach*, Gait (ed.), IRL Press, Washington D.C. (1984); Froehler, et al., Tetrahedron Lett., 27:469-472 (1986); Froehler, et al., Nucleic Acids Res., 14:5399-5407 (1986); Sinha, et al. Tetrahedron Lett., 24:5843-5846 (1983); and Sinha, et al., Nucl. Acids Res., 12:4539-4557 (1984) which are incorporated herein by reference.

In one preferred embodiment, the target nucleic acid is circular DNA. In one aspect, the circular DNA is sequenced by strand displacement synthesis. As is shown in FIG. 8, randomly-sheared fragments of genomic DNA are purified from a sample organism. The DNA 300 is then treated with for example, T4 DNA polymerase, to generate blunt ends and a single "A" nucleotide is added to the 3'-ends with for example, Taq DNA polymerase, and dATP. A mixture of two double-stranded oligonucleotide adaptors 301 and 302 (each with a "T" nucleotide on one 3'-end to complement the "A" nucleotide on the randomly-sheared fragment) is ligated to the DNA fragments 300 with T4 DNA ligase, wherein the first adaptor 301 is 5'-biotinylated on one strand and the second adaptor 302 is not biotinylated. Whereas the adaptors attach with equal probability to the DNA fragment ends, about half of the ligated DNA molecules will have one biotinylated adaptor and one non-biotinylated adaptor, one quarter will have two biotinylated adaptors, and one quarter will have two non-biotinylated adaptors as shown in FIG. 8. The desired ligated DNA fragment types, having one biotinylated and one non-biotinylated adaptor, are purified after ligation using gel electrophoresis and streptavidin-coated magnetic beads as follows.

Figure 9:
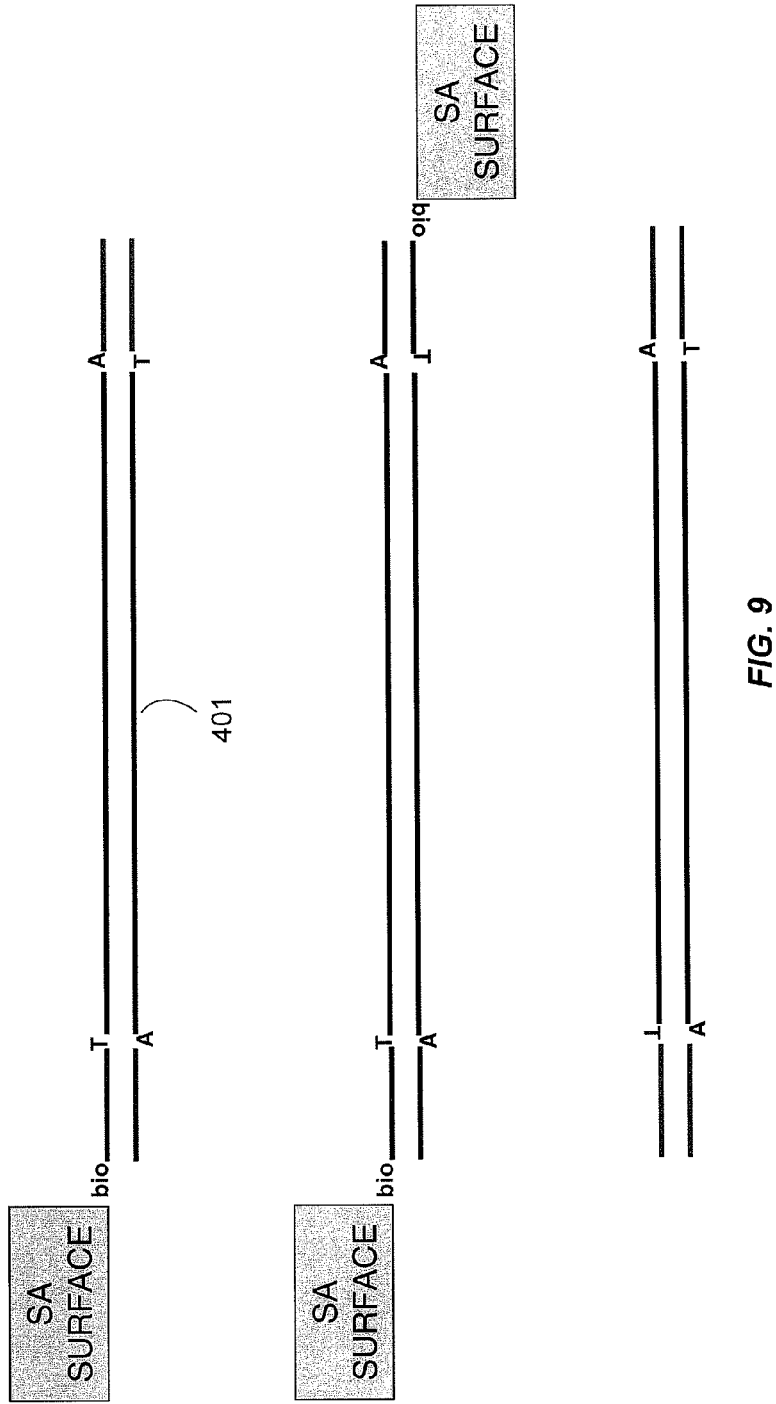
FIG. 9 illustrates a nucleic acid sample preparation of the present invention.
Figure 10:
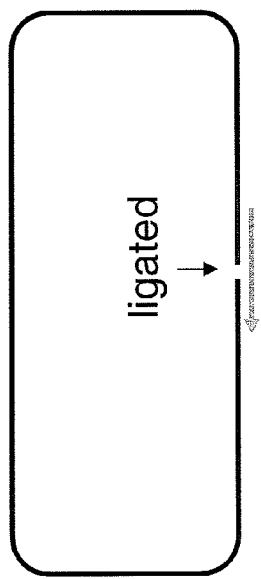
FIG. 10 illustrates a nucleic acid sample preparation of the present invention.

After ligation, DNA fragments in the size range of about 17-23 kb are purified by gel electrophoresis. As shown in FIG. 9, the purified fragments are bound to streptavidin-coated magnetic beads (Dynal). After binding, the beads are washed to remove unbound DNA. Then the bound DNA is denatured at alkaline pH and the unbiotinlyated strands 401 are eluted and the DNA still bound to the beads is discarded. As shown in FIG. 10, the eluted strands are circularized by hybridizing to a primer oligonucleotide complementary to both adaptors and ligating the two ends of the eluted strand.

C. Immobilization of the PNACs

In certain embodiments, the PNAC arrays of the present invention are immobilized on a support. Preferably, the support (e.g., solid support) comprises a bioreactive moiety or bioadhesive layer. The support can be for example, glass, silica, plastic or any other conventionally material that will not create significant noise or background for the detection methods. The bioadhesive layer can be an ionic adsorbent material such as gold, nickel, or copper, protein-adsorbing plastics such as polystyrene (U.S. Pat. No. 5,858,801), or a covalent reactant such as a thiol group.

The PNAC arrays of the present invention can be immobilized on a support in a random fashion (e.g., random X or Y position coordinates), uniform fashion (e.g., regularly spaced X or Y position coordinates) or a combination thereof. As is shown in FIG. 11, in one aspect, the PNAC are isolated into single molecule configuration. This single molecule isolation enables efficient attachment of the PNACs to the support. In addition, it allows for efficient single molecule sequencing. Advantageously, the present invention provides single PNACs attached so as to be optically resolvable from their nearest neighbor PNACs. Thus, the PNACs can be analyzed individually without interference from overlapping optical signals from neighboring PNACs. In the present invention, many individual optically resolved PNACs can be sequenced simultaneously.

Figure 12:
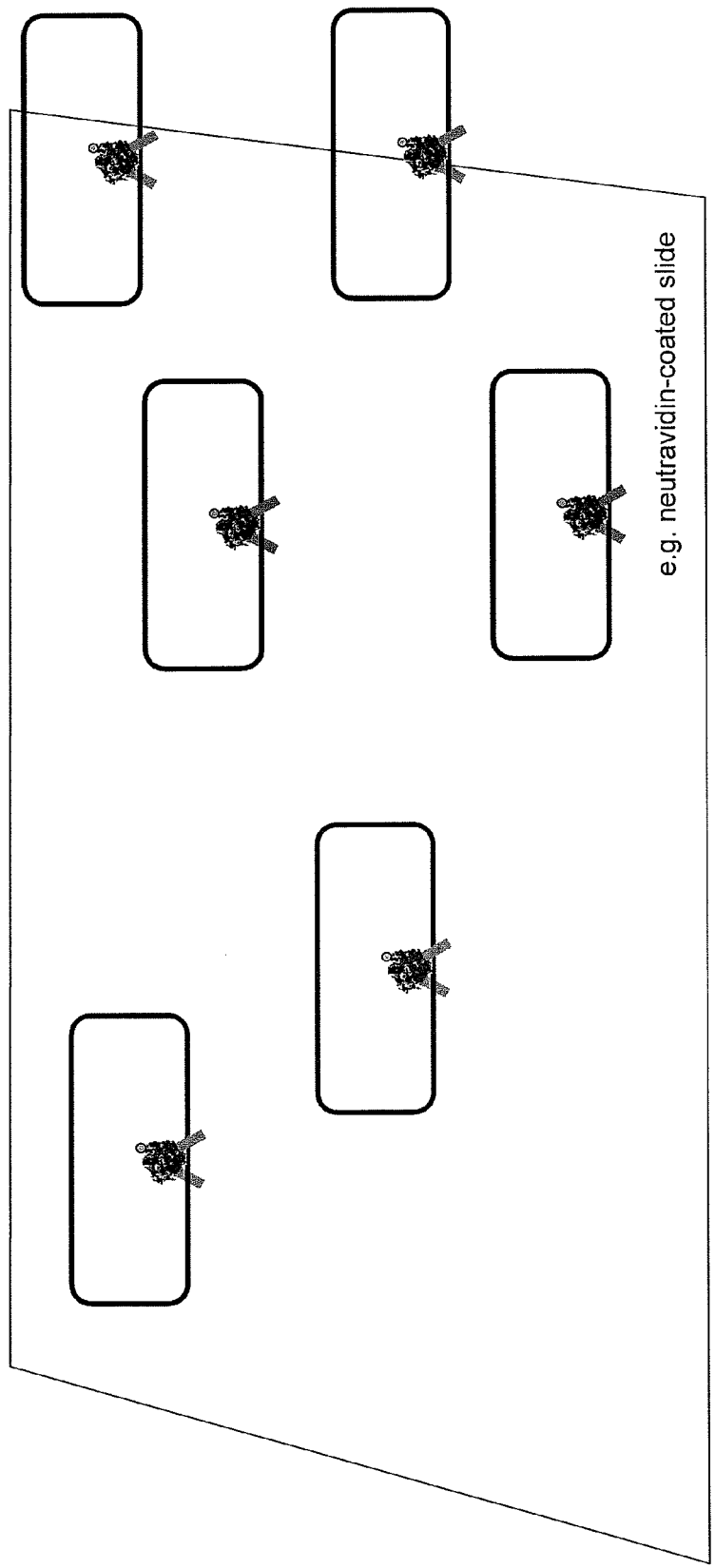
FIG. 12 illustrates a single molecule bound to a cover slip.

FIG. 12 is an example of a randomly associated array of PNACs immobilized on a neutravidin-coated slide. This diagram is merely an illustration and should not limit the scope of the claims herein. One of ordinary skill in the art will recognize other variations, modifications, and alternatives. As shown therein, PNACs are attached or immobilized to a neutravidin-coated slide via an anchor having for example, the first member of a binding pair, wherein the anchor comprises a biotin moiety. In operation, multiple sites can be sequenced with ease.

In yet another example, the PNACs can be attached to the bioadhesive pattern by providing a polyhistidine tag on the polymerase that binds to metal bioadhesive patterns. To create a patterned or random array of a bioadhesive layer, an electron-sensitive polymer such as polymethyl methacrylate (PMMA) coated onto the support is etched in any desired pattern using an electron beam followed by development to remove the sensitized polymer. The holes in the polymer are then coated with a metal such as nickel, and the polymer is removed with a solvent, leaving a pattern of metal posts on the substrate. This method of electron beam lithography provides the very high spatial resolution and small feature size required to immobilize just one molecule at each point in the patterned array. An alternate means for creating high-resolution patterned arrays is atomic force microscopy. A third means is X-ray lithography.

Other conventional means for attachment employ homobifunctional and heterobifunctional crosslinking reagents. Homobifunctional reagents carry two identical functional groups, whereas heterobifunctional reagents contain two dissimilar functional groups to link the biologics to the bioadhesive. A vast majority of the heterobifunctional cross-linking agents contain a primary amine-reactive group and a thiol-reactive group. Covalent crosslinking agents are selected from reagents capable of forming disulfide (S—S), glycol (—CH(OH)—CH(OH)—), azo (—N=N—), sulfone (—S(=O$_2$—), ester (—C(=O)—O—), or amide (—C(=O)—N—) bridges.

A bioresist layer may be placed or superimposed upon the bioadhesive layer either before or after attachment of the biologic to the bioadhesive layer. The bioresist layer is any material that does not bind the biologic. Examples include bovine serum albumin, neutravidin, gelatin, lysozyme, octoxynol, polysorbate 20 (polyethenesorbitan monolaurate) and polyethylene oxide containing block copolymers and surfactants (U.S. Pat. No. 5,858,801). Deposition of the layers is done by conventional means, including spraying, immersion and evaporative deposition (metals).

III. Methods

The present invention provides inter alia, methods to detect incorporation of a detectably labeled nucleotide phosphate such as a nucleotide triphosphate ("NTP") onto the growing end of a primer nucleic acid molecule. The method is used, for example, to genotype and sequence a nucleic acid. In turn, the sequence identification can be used to identify metabolic differences in patient groups based upon genetic polymorphism to provide improved dosing regimens, enhancing drug efficacy and safety. Further, understanding the genetic basis of disease in animal and plants will help engineer disease resistant animals & crops as well as enhance desirable characteristics.

Figure 13:
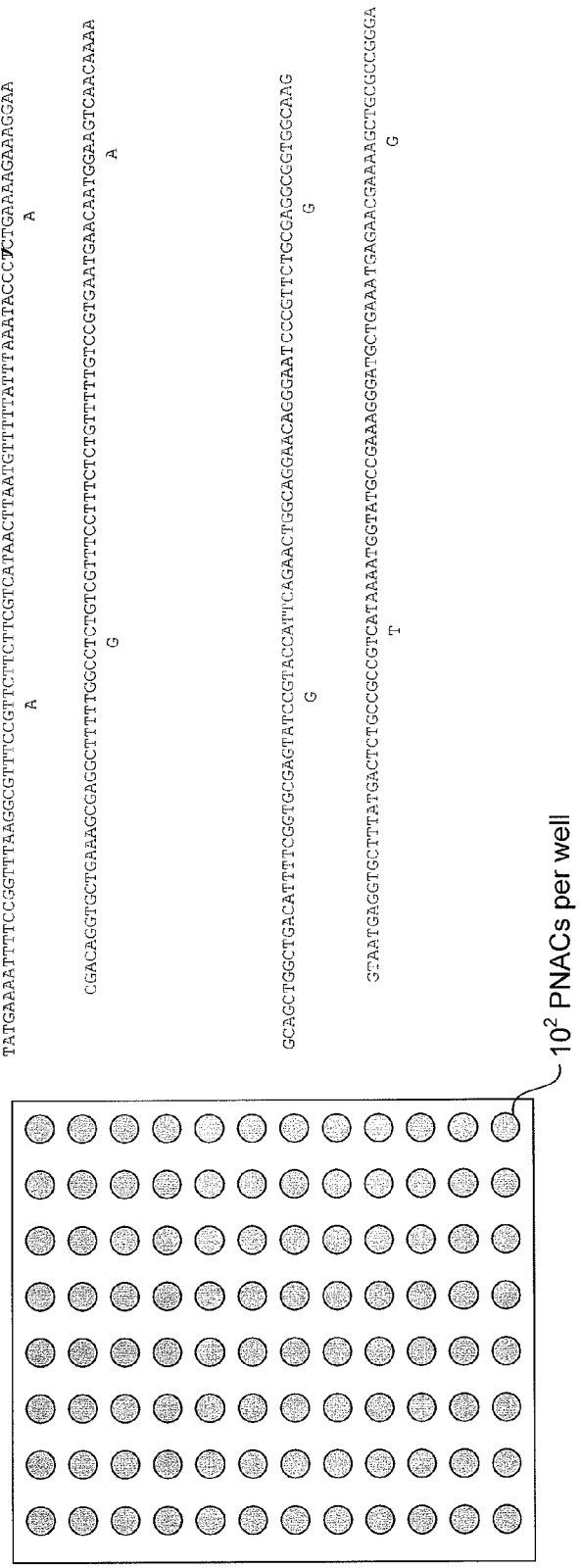
FIG. 13 illustrates a multiple sequencing embodiment of the present invention (SEQ ID NOS:12-15).

In a preferred embodiment, the methods described herein detect the "residence time" of an individual fluorogenic NP molecule on a PNAC preferably comprised of at least one RNA or DNA dependent polymerase, a single target nucleic acid template, and a single primer nucleic acid. The NPs are preferably of Formula II, which NP has a labeled γ-phosphate. As shown in FIG. 13, as the polymerase moves along the target nucleic acid, the nucleotide sequence is read by identifying the order and identity of incorporated NPs. In one embodiment, all the NPs have the same label, but each class of labeled NPs is sequentially added to the complex; the incorporated NP corresponds to the particular class that is being infused.

In one aspect, the present invention provides a method for detecting incorporation of at least one nucleotide phosphate into a single primer nucleic acid molecule, the method comprising:
 i. immobilizing onto a support a polymerase nucleic acid complex comprising a target nucleic acid, a primer nucleic acid which complements a region of the target nucleic acid, and at least one nucleic acid polymerase;
 ii. contacting the immobilized complex with at least one type of labeled nucleotide phosphate of Formula II; and
 iii. detecting the incorporation of said at least one type of labeled NP into a single molecule of said primer, while said at least one type of labeled NP is in contact with said immobilized complex, by detecting the label of the NP while said at least one type of labeled NP is in contact with said polymerase nucleic acid complex.

In one aspect, the polymerase nucleic acid complex is contacted with a single type of labeled NP. In other aspects, the polymerase nucleic acid complex is contacted with at least two different types of NPs, preferably wherein each type of NP is uniquely labeled. In still other aspects, the polymerase nucleic acid complex is contacted with at least four different types of NPs, and wherein each type of NP is uniquely labeled.

In certain aspect, the present invention provides a wherein one or more NPs are bound to a single nucleic acid molecule, such as by an intercalation complex.

In another embodiment, at least two classes of NP are used, or at least three classes of NP are used, or at least four classes of NP are used each of which is uniquely labeled. The identity of the NP incorporated during a particular incorporation event is determined by detecting the unique label of the incorporated NP, based on the residence time or the time-averaged intensity of the labeled NP in contact with the PNAC.

The NPs can optionally include a fluorescence quencher attached to either the base sugar, dye, polymerase, or combinations thereof, which quenches the fluorescence of the fluorescent dye while the NP (γ-label) is free in solution. The fluorescence associated with the immobilized complex is detected. Upon interaction with the complex, the fluorescence of the labeled NP changes (e.g., increases), as the conformation of the NP is altered by interaction with the complex, and/or as the PPi is cleaved prior to being released into the medium. The optical properties of the pyrophosphate-dye moiety change, either by conformational changes of the NP or cleavage of the PPi, which in turn facilitates detection of the fluorescent dye.

A. Miscellaneous Reaction Reagents.

The primers (DNA polymerase) or promoters (RNA polymerase) are synthetically made using conventional nucleic acid synthesis technology. The complementary strands of the probes are conveniently synthesized on an automated DNA synthesizer, e.g. an Applied Biosystems, Inc. (Foster City, Calif.) model 392 or 394 DNA/RNA Synthesizer, using standard chemistries, such as phosphoramidite chemistry, e.g. disclosed in the following references: Beaucage and Iyer, *Tetrahedron*, 48: 2223-2311 (1992); Molko et al, U.S. Pat. No. 4,980,460; Koster et al., U.S. Pat. No. 4,725,677; Caruthers et al., U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the resulting oligonucleotides are compatible with the polymerase. They can be ordered commercially from a variety of companies which specialize in custom oligonucleotides.

Primers in combination with polymerases are used to sequence target DNA. Primer length is selected to provide for hybridization to complementary template DNA. The primers will generally be at least 10 bp in length, usually at least between 15 and 30 bp in length. Primers are designed to hybridize to known internal sites on the subject target DNA. Alternatively, the primers can bind to synthetic oligonucleotide adaptors joined to the ends of target DNA by a ligase.

Similarly where promoters are used, they can be internal to the target DNA or ligated as adaptors to the ends.

B. Reaction Conditions.

The reaction mixture for the sequencing using the PNACs and methods of the present invention comprises an aqueous buffer medium which is optimized for the particular polymerase. In general, the buffer includes a source of monovalent ions, a source of divalent cations and a buffering agent. Any convenient source of monovalent ions, such as KCl, K-acetate, $NH_4$-acetate, K-glutamate, $NH_4Cl$, ammonium sulfate, and the like may be employed, where the amount of monovalent ion source present in the buffer will typically be present in an amount sufficient to provide for a conductivity in a range from about 500 to 20,000, usually from about 1000 to 10,000, and more usually from about 3,000 to 6,000 microhms.

The divalent cation may be magnesium, manganese, zinc and the like, where the cation will typically be magnesium. Any convenient source of magnesium cation may be employed, including $MgCl_2$, Mg-acetate, and the like. The amount of Mg ion present in the buffer may range from 0.5 to 20 mM, but will preferably range from about 1 to 12 mM, more preferably from 2 to 10 mM and will ideally be about 5 mM.

Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.6 at 25° C. Other agents which may be present in the buffer medium include chelating agents, such as EDTA, EGTA and the like.

C. Sample Housing.

The support is optionally housed in a flow chamber having an inlet and outlet to allow for renewal of reactants which flow past the immobilized moieties. The flow chamber can be made of plastic or glass and should either be open or transparent in the plane viewed by the microscope or optical reader. Electro-osmotic flow requires a fixed charge on the solid support and a voltage gradient (current) passing between two electrodes placed at opposing ends of the solid support. The flow chamber can be divided into multiple channels for separate sequencing. Examples of micro flow chambers exist. For example, Fu et al. (*Nat. Biotechnol.* (1999) 17:1109) describe a microfabricated fluorescence-activated cell sorter with 3 µm×4 µm channels that utilizes electro-osmotic flow for sorting.

D. Detection of Fluorophores.

Various detectors are suitable for use in the present invention. These include, but are not limited to, an optical reader, a high-efficiency photon detection system, a photodiode, a camera, a charge couple device, an intensified charge couple device, a near-field scanning microscope, a far-field confocal microscope, a microscope that detects wide-field epi-illumination, evanescent wave excitation and a total internal reflection fluorescence microscope. In certain aspects, the detection requires the imaging of single molecules in a solution. There are a variety of known ways of achieving this goal, including those described in: Basche et al., eds., 1996, "Single molecule optical detection, imaging, and spectroscopy," Weinheim et al., "Single-molecule spectroscopy," *Ann. Rev. Phys. Chem.* 48: 181-212; Soper et al., "Detection and Identification of Single Molecules in Solution," *J. Opt. Soc. Am.* B, 9(10): 1761-1769, October 1992; Keller et al. (1996), *Appl. Spectrosc.* 50: A12-A32; Goodwin et al. (1996), *Accounts Chem. Res.* 29: 607-613; Rigler (1995). *J. Biotech.,* 41: 177; Rigler et al. Fluorescence Spectroscopy; Wolfbeis O, S., Ed.; Springer, Berlin, 1992, pp 13-24; Edman et al. (1996) *Proc. Natl. Acad. Sci. USA* 93: 6710; Schmidt et al. (1996) *Proc. Natl. Acad. Sci. USA* 1 93: 2926; Keller et al. (1996) *Appl. Spectroscopy* 50: A12.

A laser source is often used as the excitation source for ultrasensitive measurements but conventional light sources such as rare gas discharge lamps and light emitting diodes (LEDs) are also used. The fluorescence emission can be detected by a photomultiplier tube, photodiode or other light sensor. An array detector such as a charge-coupled device (CCD) detector can be used to image an analyte spatial distribution.

Raman spectroscopy can be used as a detection method for microchip devices with the advantage of gaining molecular vibrational information. Sensitivity has been increased through surface enhanced Raman spectroscopy (SERS) effects but only at the research level. Electrical or electrochemical detection approaches are also of particular interest for implementation on microchip devices due to the ease of integration onto a microfabricated structure and the potentially high sensitivity that can be attained. The most general approach to electrical quantification is a conductometric measurement, i.e., a measurement of the conductivity of an ionic sample. The presence of an ionized analyte can correspondingly increase the conductivity of a fluid and thus allow quantification. Amperiometric measurements imply the measurement of the current through an electrode at a given electrical potential due to the reduction or oxidation of a molecule at the electrode. Some selectivity can be obtained by controlling the potential of the electrode but it is minimal. Amperiometric detection is a less general technique than conductivity because not all molecules can be reduced or oxidized within the limited potentials that can be used with common solvents. Sensitivities in the 1 nM range have been demonstrated in small volumes (10 nL). The other advantage of this technique is that the number of electrons measured (through the current) is equal to the number of molecules present. The electrodes required for either of these detection methods can be included on a microfabricated device through a photolithographic patterning and metal deposition process. Electrodes could also be used to initiate a chemiluminescence detection process, i.e., an excited state molecule is generated via an oxidation-reduction process which then transfers its energy to an analyte molecule, subsequently emitting a photon that is detected.

Acoustic measurements can also be used for quantification of materials but have not been widely used to date. One method that has been used primarily for gas phase detection is the attenuation or phase shift of a surface acoustic wave (SAW). Adsorption of material to the surface of a substrate where a SAW is propagating affects the propagation characteristics and allows a concentration determination. Selective sorbents on the surface of the SAW device are often used. Similar techniques may be useful in the methods described herein.

In certain embodiments, the methods of the present invention involve detection of laser activated fluorescence using microscope equipped with a camera. It is sometimes referred to as a high-efficiency photon detection system. Nie et. al. (1994), "Probing individual molecules with confocal fluorescence microscopy," *Science* 266:1018-1019.

The detection of single molecules involves limiting the detection to a field of view in which one has a statistical reason to believe there is only one molecule (homogeneous assays) or to a field of view in which there is only one actual point of attachment (heterogeneous assays). The single-molecule fluorescence detection of the present invention can be practiced using optical setups including near-field scanning microscopy, far-field confocal microscopy, wide-field epi-illumination, and total internal reflection fluorescence (TIRF) microscopy. For two-dimensional imaging fluorescence detection, the microscope is typically a total internal reflectance microscope. Vale et. al., 1996, Direct observation of single kinesin molecules moving along microtubules, *Nature* 380: 451, Xu and Yeung 1997, Direct Measurement of Single-Molecule Diffusion and Photodecomposition in Free Solution, *Science* 275: 1106-1109.

Suitable radiation detectors include may be, for example, an optical reader, photodiode, an intensified CCD camera, or a dye-impregnated polymeric coating on optical fiber sensor. In a preferred embodiment, an intensified charge couple device (ICCD) camera is used. The use of a ICCD camera to image individual fluorescent dye molecules in a fluid near the surface of the glass slide is advantageous for several reasons. With an ICCD optical setup, it is possible to acquire a sequence of images (movies) of fluorophores. In certain aspects, each of the NTPs of the present invention has a unique fluorophore associated with it, as such, a four-color instrument can be used having four cameras and four excitation lasers. Thus, it is possible to use this optical setup to sequence DNA. In addition, many different DNA molecules spread on a microscope slide can be imaged and sequenced simultaneously. Moreover, with the use of image analysis algorithms, it is possible to track the path of single dyes and distinguish them from fixed background fluorescence and from "accidentally dequenched" dyes moving into the field of view from an origin upstream.

In certain aspects, the preferred geometry for ICCD detection of single-molecules is total internal reflectance fluorescence (TIRF) microscopy. In TIRF, a laser beam totally reflects at a glass-water interface. The optical field does not end abruptly at the reflective interface, but its intensity falls off exponentially with distance. The thin "evanescent" optical field at the interface provides low background and enables the detection of single molecules with signal-to-noise ratios of 12:1 at visible wavelengths (see, M. Tokunaga et al., *Biochem. and Biophys. Res. Comm.* 235, 47 (1997) and P. Ambrose, *Cytometry*, 36, 244 (1999)).

The penetration of the field beyond the glass depends on the wavelength and the laser beam angle of incidence. Deeper penetrance is obtained for longer wavelengths and for smaller angles to the surface normal within the limit of a critical angle. In typical assays, fluorophores are detected within about 200 nm from the surface which corresponds to the contour length of about 600 base pairs of DNA. Preferably, a prism-type TIRF geometry for single-molecule imaging as described by Xu and Yeung is used (see, X-H. N. Xu et al., *Science*, 281, 1650 (1998)).

Single molecule detection can be achieved using flow cytometry where flowing samples are passed through a focused laser with a spatial filter used to define a small volume. U.S. Pat. No. 4,979,824 describes a device for this purpose. U.S. Pat. No. 4,793,705 describes and claims in detail a detection system for identifying individual molecules in a flow train of the particles in a flow cell. The '705 patent further describes methods of arranging a plurality of lasers, filters and detectors for detecting different fluorescent nucleic acid base-specific labels. U.S. Pat. No. 4,962,037 also describes a method for detecting an ordered train of labeled nucleotides for obtaining DNA and RNA sequences using a nuclease to cleave the bases rather than a polymerase to synthesize as described herein. Single molecule detection on solid supports is described in Ishikawa, et al. (1994) Single-molecule detection by laser-induced fluorescence technique with a position-sensitive photon-counting apparatus, *Jan. J. Apple. Phys.* 33:1571-1576. Ishikawa describes a typical apparatus involving a photon-counting camera system attached to a fluorescence microscope. Lee et al. (1994), Laser-induced fluorescence detection of a single molecule in a capillary, *Anal. Chem.*, 66:4142-4149 describes an apparatus for detecting single molecules in a quartz capillary tube. The selection of lasers is dependent on the label and the quality of light required. Diode, helium neon, argon ion, argon-krypton mixed ion, and Nd:YAG lasers are useful in this invention.

Detecting the fluorophore can be carried out using a variety of mechanisms. These mechanisms include for example, fluorescence resonance energy transfer, an electron transfer mechanism, an excited-state lifetime mechanism and a ground-state complex quenching mechanism.

E. Labeled NTP Residence Times.

The residence time of a correctly paired NTP (i.e., an NTP that is complementary to the first unpaired nucleotide residue of the target NA that is just downstream from the extending end of the primer NA) is significantly longer than the residence time of an incorrectly paired NTP.

The kinetic mechanism has been well characterized for the reaction catalyzed by the T7 DNA polymerase. Patel et al. (1991), *Biochemistry* 30:511; Wong et al., *Biochemistry* 30:526. In this reaction, the polymerase/target NA/primer NA complex is first contacted by an NTP. When a "correct" NTP (i.e., complementary to the template nucleotide in the enzyme active site) binds, the enzyme pocket "closes" on the nucleotide and then the coupling chemistry occurs. The enzyme "opens" back up, releases the PPi formerly attached to the NTP, and the enzyme translocates to the next base on the template. An incorrect NTP (i.e., not complementary to the template base) has a very short residence time on the enzyme. See, e.g., kinetic data at Table II of Patel et al. (1991), *Biochemistry* 30:511. In this instance and under the polymerization conditions used, the difference between an incorporated NTP residence time is about 100 times longer to about 10,000 times longer than the residence time of an NTP that is not incorporated. In certain aspects, the residence time of an NTP that is incorporated into the primer nucleic acid is at least about 200 times longer to about 500 times longer such as 250, 350 or 450 times longer than the residence time of an NTP that is not incorporated.

The relatively long residence time of a correct NTP is used in the present invention to detect the interaction of a correct NTP with an immobilized polymerase/primer NA/template NA complex. Depending on the incubation conditions (e.g., salt concentration, temperature, pH, etc.), the residence time of a nucleotide that is incorporated into an elongating primer is longer than the residence time of an NTP that is not incorporated. The residence time of the label of a correct labeled NTP that is incorporated into the elongating primer ranges from about 1.0 milliseconds to about 100 milliseconds, preferably, from about 2.0 milliseconds to about 10 milliseconds. In certain instances, the accuracy of the residence time of the measurement depends on the speed of the detector.

IV. EXAMPLES

Example 1

Introduce a Unique Cysteine on the Protein Surface for Attaching a Fluorophore A unique cysteine amino acid is placed on the surface of Therminator polymerase to attach the fluorescent probe. This is accomplished by site-directed mutation of the Therminator gene in two steps. First, the single native surface-exposed cysteine, C223, is eliminated by mutation to serine, resulting in the mutant C223S. Mutant C223S has no surface-exposed cysteines. Next, a new cysteine is uniquely placed on the protein surface by constructing the mutant E554C. The new cysteine is located on the rim of a cleft in the protein, near the location of a quencher on a bound nucleotide. The resulting mutant is C223S:E554C.

Example 2

Add Histidine Patches to the Protein Surface Attaching Anchors

Two histidine patches are engineered onto the surface of the C223S:E554C Therminator protein by making the multiple mutations D50H:T55H:E189H:R196H:K229H. The resulting mutant, C223S:E554C:D50H:T55H:E189H:R196H:K229, is called "ThioHis".

Example 3

Circularization of Target DNA

Randomly-sheared fragments of genomic DNA is purified from the sample organism. The DNA is treated with T4 DNA polymerase to generate blunt ends and a single "A" nucleotide is added to the 3'-ends with Taq DNA polymerase and dATP.

A mixture of two double-stranded oligonucleotide adaptors is ligated to the DNA fragments with T4 DNA ligase.

```
First adaptor (SEQ ID NOS: 17 and 18):
Biotin-CGCCACATTACACTTCCTAACACGT
       GCGGTGTAATGTGAAGGATTGTGC Second adaptor (SEQ ID NOS: 19 and 20):
CAGTAGGTAGTCAAGGCTAGAGTCT
GTCATCCATCAGTTCCGATCTCAG Ligated DNA products:
genomic DNA: lower case
adaptors: upper case, (p) 5'-phosphate
italicized: DNA strand recovered after elution at alkaline pH Product 1 (SEQ ID NOS: 21-24)
Bio-CGCCACATTACACTTCCTAACACGTnnnnn...nnnnnaGACTCTAGCCTTGACTACCTACTGAAA-3'
    GCGGTGTAATGTGAAGGATTGTGCannnnn...nnnnnTCTGAGATCGGAACTGATGGATGACp-5'

Product 2 (SEQ ID NOS: 21, 25, 26 and 24)
Bio-CGCCACATTACACTTCCTAACACGTnnnnn...nnnnnaCGTGTTAGGAAGTGTAATGTGGCG-3'
 3'-GCGGTGTAATGTGAAGGATTGTGCannnnn...nnnnnTGCACAATCCTTCACATTACACCGC-Bio Product 3 (SEC ID NOS:27, 22, 23 and 28)
  5'-pCAGTAGGTAGTCAAGGCTAGAGTCTnnnnn...nnnnnaGACTCTAGCCTTGACTACCTACTGAAA-3'
 3'-AAAGTCATCCATCAGTTCCGATCTCAGannnnn...nnnnnTCTGAGATCGGAACTGATGGATGACp-5'
```

After ligation, DNA fragments in the size range of about 17-23 kb are purified by gel electrophoresis. The purified fragments are bound to streptavidin-coated magnetic beads (Dynal). After binding, the beads are washed to remove unbound DNA. Then the bound DNA is denatured at alkaline pH and the unbiotinlyated strands are eluted (see above; Product 1, italicized font), and the DNA still bound to the beads is discarded. The eluted strands are circularized by hybridization to a primer oligo complementary to both adaptors (SEQ ID NO:30):

```
Primed circular template (SEQ ID NO: 29)
stars mark the ligation site:       **
5'-...nnnnnCGTGTTAGGAAGTGTAATGTGGCGCAGTAGGTAGTCAAGGCTAGAGTCTnnnnn...-3'  (template strand)

3'-GCACAATCCTTCACATTACACCGCGTCATCCATCAGTTCCGATCTCAGA-5'        (primer)
```

Example 4

Protein Modifications

The ThioHis Therminator mutant protein (Example 2) is conjugated to tetramethylrhodamine-5-maleimide (Molecular Probes) at position C554. Anchors (biotin-X nitrilotriacetic acid, Molecular Probes) are added to bind to the two histidine patches and the modified protein is purified.

Example 5

Anchor Protein-DNA Complexes to Glass Coverslips

The modified ThioHis protein (Example 4) is mixed with the primed circular template DNA (Example 3) to form polymerase-DNA complexes. The complexes are added to a streptavidin-coated glass coverslip to topologically trap the DNA between the protein and the glass surface. The coverslip is washed prior to sequencing the immobilized DNA.

Example 6

Synthesis Of dUTP-γ-TMR

A. Synthesis of dUTP-γS dUDP (16 mg, 40 μmol; Sigma D-3626) and ATP-3S (44 mg, 80 μmol; Boehringer Mannheim 102342) were dissolved in 10 mL of (20 mM Tris-Cl pH 7.0, 5% glycerol, 5 mM dithiothreitol, 5 mM $MgCl_2$). Nucleoside diphosphate kinase (0.5 mL, 5000 units; Sigma N-0379) was added and the sample was incubated at 37° C. for 2 h to equilibrate the γ-thiophosphate moiety between the uridine and adenosine nucleotides. As expected from the reactant stoichiometry, 2/3 of the dUDP was converted to dUTP-γS. The product was purified by reversed-phase HPLC using a linear gradient of 0% to 100% Buffer B mixed into Buffer A (Buffer A is 0.1 M triethylammonium acetate in water, pH 7, 4% acetonitrile; Buffer B is the same as Buffer A with 80% acetonitrile).

B. Synthesis of dUTP-γ-TMR dUTP-γS (45 μg, 90 nmol; from step a) was dissolved in 295.5 μL of (20 mM sodium phosphate pH 7.5, 33% dimethylformamide). BODIPY TMRIA (4.5 μL, 0.45 μmol dissolved in dimethylformamide; Molecular Probes) was added and the sample was held in the dark at room temperature for 2.5 h. The product was obtained in 90% yield and was purified by reversed-phase HPLC as in step a.

Example 7

Strep-Tag II T7 DNA Polymerase

The T7 DNA polymerase gene was amplified from T7 phage DNA using the forward primer (SEQ ID NO:31)

```
5'-ATGATCGTTTCTGCCATCGCAGCTAAC (encodes the exonuclease mutations
A14-to-C14 and A20-to-C20)
and the reverse primer SEQ ID NO: 32)

5'-TCAGTGGCAAATCGCC.
```

An oligonucleotide (SEQ ID NO:33) encoding the Strep-Tag II sequence overlapping the 5'-end of the amplified T7 exo-polymerase gene (SEQ ID NO:34) was synthesized on an automated oligonucleotide synthesizer:

```
5'-ATGTCCAACTGGTCCCACCCGCAGTTCGAAAAAGGTGGAGGTTCCGCT
    M  S  N  W  S  H  P  Q  F  E  K  G  G  G  S  A
           Strep-Tag II Peptide              Spacer ATGATCGTTTCTGCCATCGCAGCTAAC..
    M  I  V  S  A  I  A  A  N....
T7 polymerase N-terminus overlap (2 exo- mutations underlined)
```

The single-stranded synthetic oligonucleotide was spliced to the amplified T7 gene (above) by overlapping PCR (Horton et al. (1989) "Site-directed mutagenesis by overlap extension using the polymerase chain reaction," *Gene* 77:61-68) using the StrepTag forward primer (SEQ ID NO:35)

```
5'-ATGTCCAACTGGTCCCACCC with the reverse primer (SEQ ID NO: 36)

5'-TCAGTGGCAAATCGCC.
```

The spliced PCR product was cloned into the pET11 plasmid vector (Stratagene), overexpressed in *E. coli* BL21(DE3) pLysS, and purified by Strep-Tag II affinity chromatography (Maier et al. (1998) *Anal. Biochem* 259: 68-73).

Example 8

Polymerase Immobilization

A. Surface Passivation with Polyethylene Glycol

Fused silica coverslips (1" square, 200 μm thick; SPI Supplies, West Chester Pa.) were cleaned by soaking overnight in chromic acid and washing in distilled water in a sonic bath (Model 2200, Branson, Danbury Conn.). Methoxy-PEG-silane MW 5,000 (Shearwater Polymers, Huntsville Ala.) was dissolved at 10 mg/ml in 95:5 ethanol:water and the pH was adjusted to 2.0 with HCl. Cleaned coverslips were immersed in the PEG solution for 2 hours, washed 3 times each in ethanol, 3 times in water, dried overnight at 70 C, washed overnight in 1% sodium dodecyl sulfate in water, washed with deionized water in an ultrasonic bath, and baked for 1 day at 70 C (Jo S, Park K. Surface modification using silanated poly(ethyleneglycol)s. Biomaterials 21: 605-616.2000).

B. Biotinylation and Streptavidin Monolayer

Photoactivatable biotin (12 µg; Pierce, Rockford Ill.) was dissolved in 1 ml of deionized water. The solution was applied to the top surface of a PEG-silane coated coverslip from step (a) and the water was evaporated under vacuum. The coverslip was exposed to UV light (General Electric Sunlamp RSM, 275W) for 20 minutes at a distance of 5 cm. The coverslip was washed with deionized water and nonspecific binding sites are blocked by overlaying a solution of 3% bovine serum albumin in 50 mM Tris-Cl pH 7.5, 150 mM NaCl (TBS) for 1 hour at room temperature. The coverslip was washed with TBS, a solution of streptavidin (1 mg/mL in TBS; Pierce, Rockford Ill.) was applied for 30 minutes, and the coverslip was washed with TBS+0.1% Tween 20 followed by TBS alone.

The streptavidin-coated coverslip from step (b) was spotted with 20 µL of T7 DNA polymerase exo⁻Strep-tag II (10 µM in TBS). After 1 hr, the coverslip was washed with TBS, ready for use.

C. Nickel Nanodots

In one embodiment, a polymerase is attached to each dot of an array of nickel nanodots. (Depending on the fluorophore used, the nickel nanodot may, however, exhibit background fluorescence, which must be corrected for.) The required equipment includes a spinner (PWM 202 E-beam resist spinner, Headway Research Inc.), an evaporator (SC4500 thermal e-gun evaporator, CVC Products Inc.), and a scanning electron microscope (Leo 982 with Nabity pattern generator, Leo Electron Microscopy Inc.).

Clean a 25 mm diameter microscope coverslip on the spinner by spraying alternately with acetone and isopropyl alcohol (IPA) and spinning the last IPA film until dry. Coat the coverslip in the spinner with 0.5 ml of PMMA (poly(methyl methylacrylate), MW 496 kDa, 2% in chlorobenzene), bake on a hotplate at 170 C for 10 min, coat with 0.5 ml of PMMA (MW 950 kDa, 2% in methyl isobutyl ketone [MIBK]), and bake again. Apply the conductive layer by evaporating 100 Angstroms of gold onto the PMMA film in the CVC SC4500. Use the electron microscope to etch the array pattern into the PMMA film using a pattern generator on the Leo 982 as specified by a CAD drawing (Design CAD, 50 nm spots, 10 µm center-to-center spacing, 200×200 dot array).

Remove the gold layer by placing the exposed coverslip in Gold Etch (15-17% sodium iodide) for 7 seconds followed by rinsing with IPA and water. Deposit Tantalum (50 Angstroms) and Nickel (100 Angstroms) on the coverslip in the CVC SC4500. Remove the PMMA in a 1:1 mix of acetone and methylene chloride for 10-15 min followed by sonication for several seconds and rinsing with IPA and water.

Attach the polymerase just before use by applying 10 µl of a 15 nM solution of polyhistidine-tagged Klenow DNA polymerase exo⁻ (prepared using TOPO cloning vector and Pro-Bond Resin, Invitrogen Inc.) in phosphate-buffered saline (PBS; Harlow E., Lane D. 1988. Antibodies A Laboratory Manual. Cold Spring Harbor Laboratory ISBN 0-87969-14-2) to the coverslip; after 20 min, wash the coverslip in PBS and use immediately.

Example 9

Determination of Cystic Fibrosis Mutant

A polymerase-coated coverslip is placed on the microscope and a 20 µl sample is applied under a water immersion objective lens. The sample contains 40 mM Tris-Cl (pH 7.5), 1 mM ethylenediaminetetraacetic acid, 1 mM dithiothreitol, 0.1 mg/ml of bovine serum albumin, 12.5 mM magnesium chloride, 10 nM dUTP-TMR, 100 nM each of dATP, dCTP, and dGTP, and 10 µg/ml of primer-template DNA. Depending on the activity of the immobilized enzymes, the nucleotide concentration may have to be adjusted so that individual incorporation events are time-resolvable. Data are collected and analyzed as described in Example 6 to determine whether the dUTP-TMR nucleotide is incorporated into the primer strand. (In order to perform this experiment in a droplet on an open coverslip as described, it may be necessary to speed the motion of free dUTP-TMR through the imaged zone by drive convection with a nitrogen stream, depending on ambient conditions. It is also necessary to use a water immersion objective lens immersed directly in the sample.) The results are compared against a control without primer-template DNA to demonstrate the appearance of longer fluorescence bursts in the test sample indicating a template sequence which supports dUTP incorporation. Two sample primer-templates are compared; they are synthetic oligonucleotides derived from the cystic fibrosis transmembrane conductance regulator gene (Welsh et al. (1993), *J. Cell Science* 106S:235-239).

```
Normal Allele (does not incorporate dUTP-γ-TMR)(SEQ ID NOS: 37 and 38)
primer    3'-CACCATTAAAGAAAATATCAT
template  5'-GUGGUAAUUUCUUUUAUAGUAG (Delta)F508 Deletion Mutant (does incorporate dUTP-γ-TMR)(SEQ ID NOS:
 37 and 39)
primer    3'-CACCATTAAAGAAAATATCAT
template  5'-GUGGUAAUUUCUUUUAUAGUAA
```

Example 10

Microscope Setup

Figure 14:
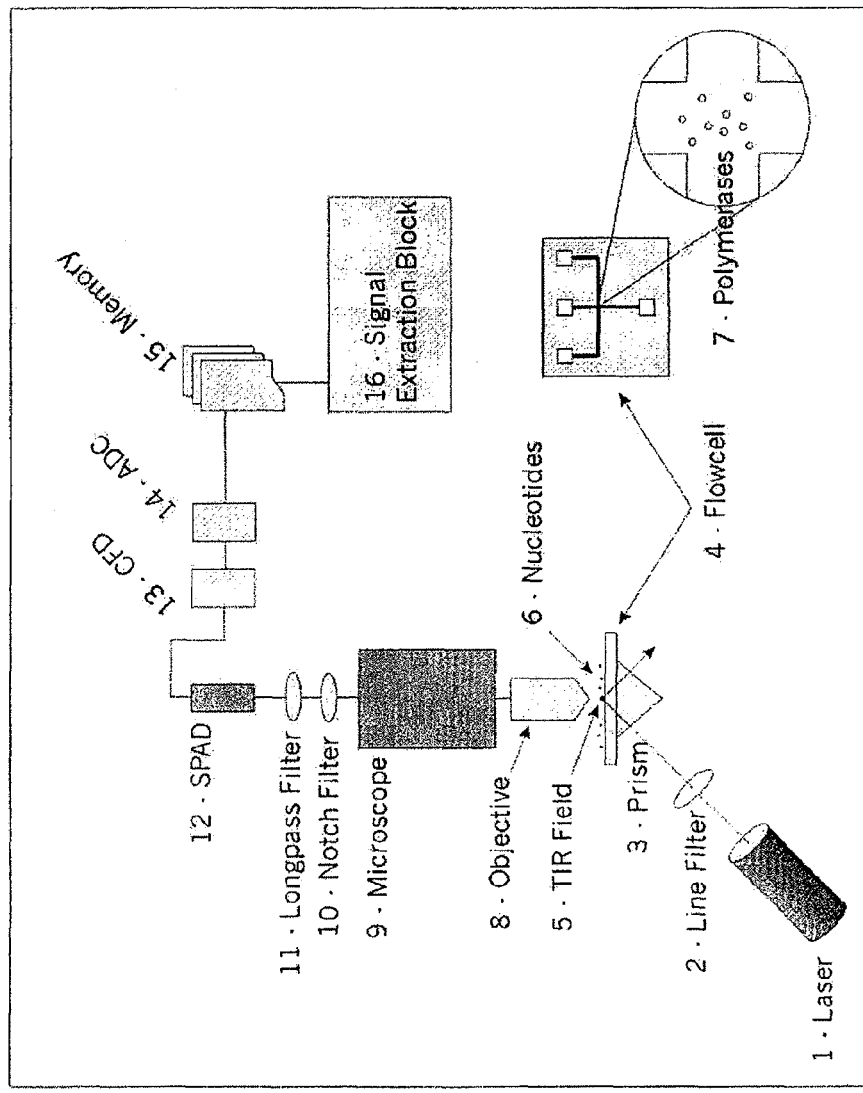
FIG. 14 illustrates a schematic view of a setup for a residence-time detector.

The setup for a residence-time detector is described in FIG. 14. A multicolor mixed-gas laser 1 emits light at tunable wavelengths. The laser beam is first passed through a laser line filter 2 and then at a right angle into a fused-silica prism 3 which is optically connected to the fused silica flowcell 4 by immersion oil. The labeled nucleotides 6 flow in a buffer solution across the polymerase enzymes immobilized on the surface of the flowcell chamber 7. Laser light strikes the fused silica-buffer interface at an angle such that the critical angle between fused-silica and the buffer solution is exceeded. The light is thus completely reflected at the interface, giving rise to a total internal reflection (TIR) evanescent field 5 in the solution. The angle is adjusted to give a 1/e penetrance of between 1 and 200 nm into the solution. The immobilized polymerases 7 are illuminated in the evanescent field and are imaged using a microscope 9 with an objective lens 8 mounted over the flowcell. Fluorescence emission at the microscope output passes through a notch filter 10 and a long pass filter 11 which allow the fluorescence emission to pass through while blocking scattered laser light. The fluorescence photons are focused onto a single-photon avalanche diode SPAD 12. Signals are processed by a constant fraction discriminator CFD 13, digitized by an analog-to-digital converter ADC 14, and stored in memory 15. Signal extraction algorithms 16 are performed on the data stored in memory. These algorithms may distinguish signal from background, filter the data, and perform other signal processing functions. The signal processing may be performed off-line in a computer, or in specialized digital signal processing (DSP) chips controlled by a microprocessor. The fluorescence is recorded using, for example by using CCD camera capable of recording single fluorophore molecules. Residence times and polymerase speed may be manipulated by controlling the reaction conditions (temperature, pH, salt concentration, labeled NTP concentration, etc.)

Example 11

Data Acquisition and Analysis

A computer model was developed to show the appearance of known (i.e., simulated) incorporation events where the nucleotide is retained by a polymerase while the base-addition chemistry occurs.

The simulation was written in MATLAB. It operates by introducing free background nucleotides into the field of view at a rate determined by the flux, which is calculated from the bias flow and optical detection volume. The detection volume is determined by the diffraction-limited focus (Airy disc diameter) and depth of the evanescent light field. The time between molecule arrivals is governed by an exponential probability distribution. As each molecule enters the simulation, the number of photons it emits is a Poisson random number, with mean calculated from the time it spends in the focal volume (determined by the bias flow), the excitation rate of the molecule (determined by the laser intensity, photon energy, and absorption cross section of the dye), and the fluorescence quantum yield of the dye. The number of photons seen by the detector is calculated in turn by the detection efficiency ratio. The photons detected are scattered in time according to a second exponential distribution, with rate calculated from the photon capture rate.

Signal molecules (i.e., nucleotides bound to the enzyme during the base-addition reaction) are introduced in time at a rate given by another simulation parameter, the reaction rate, and again distributed by a separate exponential distribution. The time a signal molecule spends in the resolution volume is determined by a random number with uniform distribution from 2 to 5 ms, consistent with the enzyme kinetics of T7 DNA polymerase (Patel S, Wong I, Johnson K (1991) Biochemistry 30: 511). The number of photons detected is a Poisson random number with mean detected as in the background molecule case. The photons detected are distributed according to the same distribution as the photons coming from background molecules.

To detect the residence-time bursts, the time arrival of all photons is discretized by a sample clock. Then the photon data is processed with a weighted sliding-sum filter, using a Hamming window. The signal energy is calculated and displayed in time. The bursts are detected by two thresholds: a signal energy threshold (vertical), and a time threshold (horizontal). A photon burst must pass both thresholds in order to be classified as a signal event.

Figure 15:
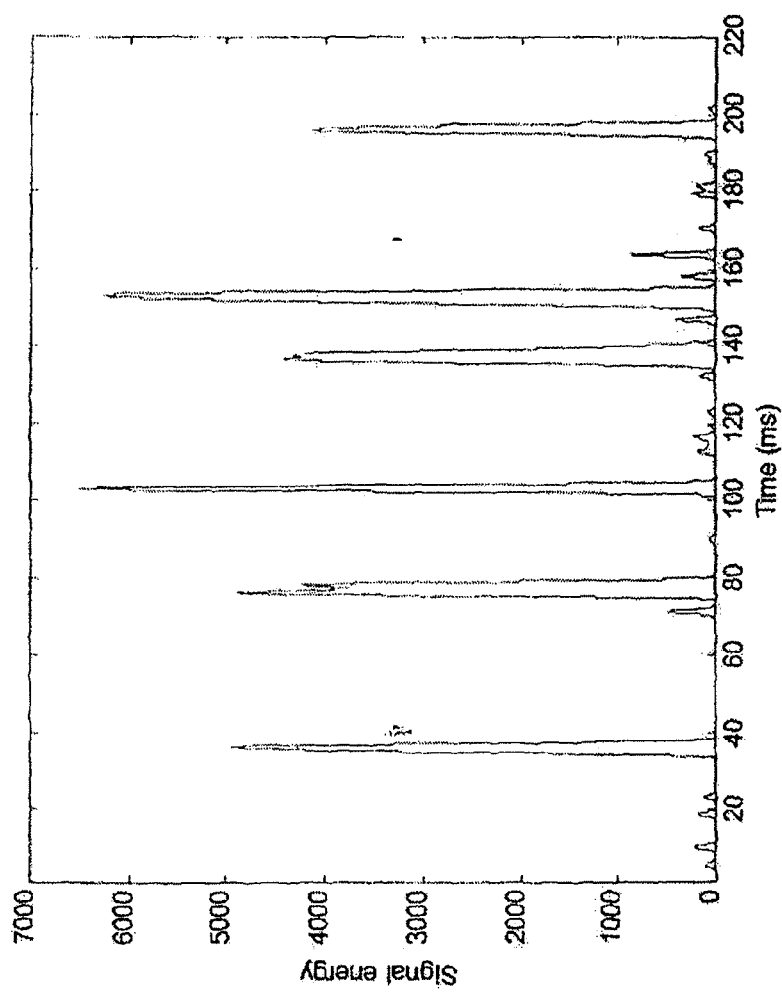
FIG. 15 illustrates a computer simulation of incorporation events detected above a signal energy threshold of 2500. The experimental parameters are summarized in Table III.
Figure 16:
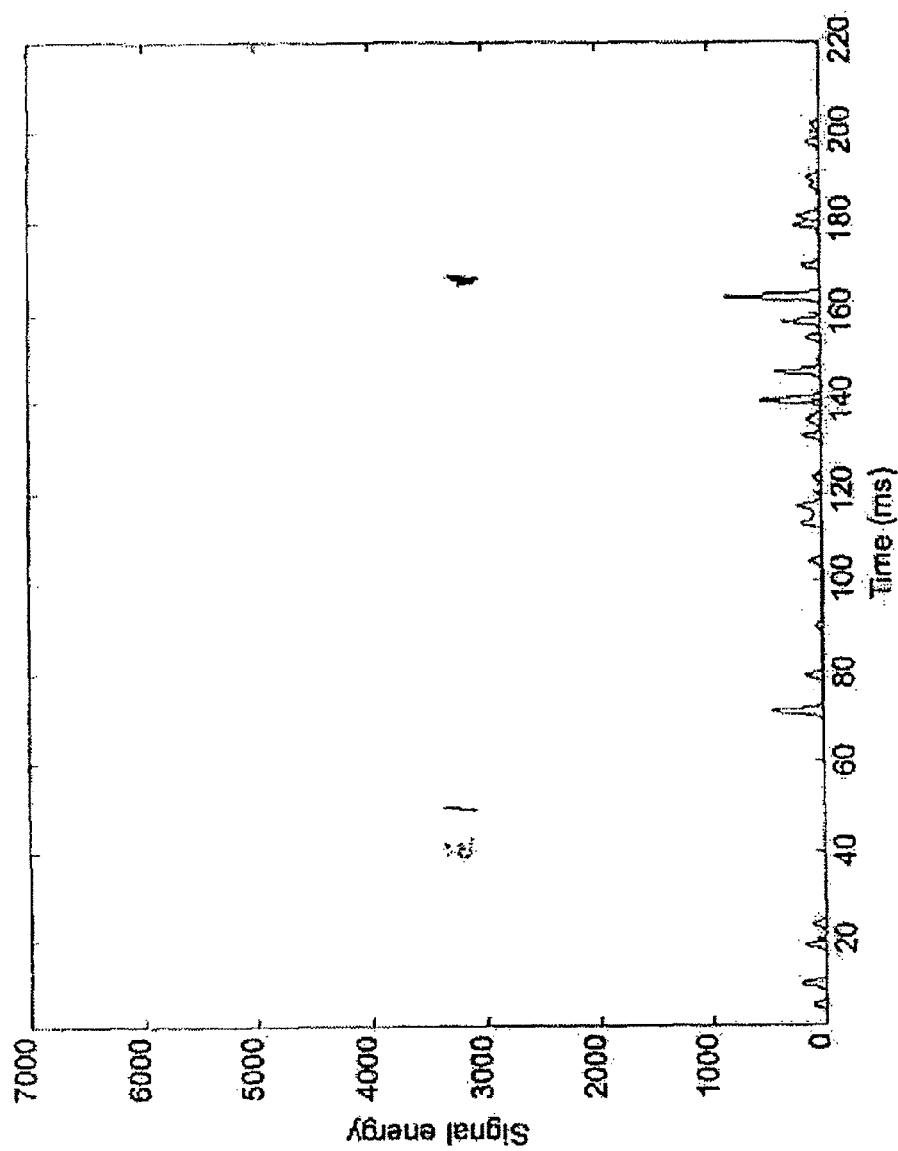
FIG. 16 illustrates a computer simulation of background incorporation using the same experimental parameters used in FIG. 15.

Two simulation results are shown in FIGS. 15 and 16. The parameters are the same between the two Figures (Table III).

TABLE III

| PARAMETER NAME | VALUE |
|---|---|
| Laser power | 150 (mW) |
| Laser spot diameter | 20 (micrometers) |
| Numerical aperture of objective lens | 1.2 |
| Evanescent light field height | 30 (nm) |
| Bias flow | 2 (mm/s) |
| Molarity | 10e−9 (mol/L) |
| Fluorescence quantum yield (for Tetramethylrhodamine, TMR) | 0.15 |
| Net detection efficiency | 3% |
| Sample clock | 1.0 (MHz) |

Example 12

This example illustrates the synthesis of a compound of the present invention.

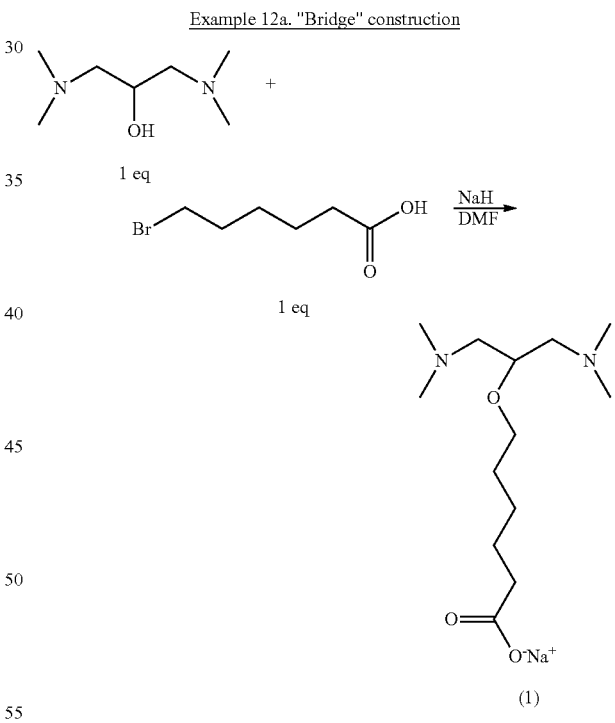

Experimental:

Sodium hydride (Aldrich, 3.85 mmol, 154 mg*) is washed with hexane to remove the mineral oil under inert atmosphere. Dry compound by continually flushing with an inert gas. Add the sodium hydride in 20 mL anhydrous DMF, which results in a slurry. 1,3-bis-(dimethylamino)-2-propanol (Aldrich, 1.54 mmol, 251 uL) was dissolved in anhydrous DMF. Add the sodium hydride slurry and the propanol solution slowly together at 0° C. under inert atmosphere. Dissolve 6-bromohexanoic acid (Aldrich, 1.54 mmol, 300 mg) in 5 mL anhydrous DMF. Add bromohexanoic acid solution to the alkoxide solution. Remove flask from ice bath and continue reaction at room temperature for 1.5 hrs. The reaction is quenched by slowly adding dry ice to the reaction mixture. Filter the reaction mixture through a glass frit, keeping filtrate. Dry filtrate and titurate with ethyl ether. Reaction monitored via C18 TLC with iodine visualization. ESI-MS [M+1] calculated 261.2. ESI-MS [M+1] observed 261.2. *The sodium hydride weighed out equates to 60% by weight of sodium hydride stored in mineral oil.

Example 12b. Iodoquinolinium compound

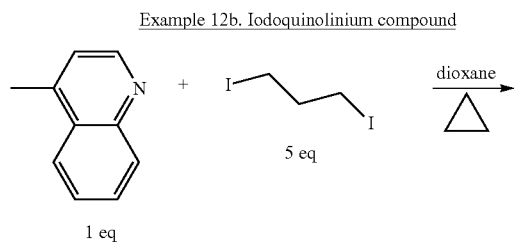

Experimental

Lepidine (Aldrich, 0.522 mmol, 69 µL) and 1,3-diiodopropane (Aldrich, 2.6 mmol, 300 µL) are added together with 3 mL of 1,4-dioxane. Solution is heated to 100° C. and allowed to react overnight. Resulting solution is dried in vacuo and recrystallized in acetone. Reaction monitored by C18 HPLC. Final crystals are placed under high vacuum to dry compound completely. ESI-MS [M+1] calculated 312.0. ESI-MS [M+1] observed 312. Stærk et al. *Bioconj. Chem.* 8(1997)869-877; Brooker et al. *J. Am. Chem. Soc.* 63(1942)199-210

Example 13c. 2-methylothio-N-methylbenzothiazolium

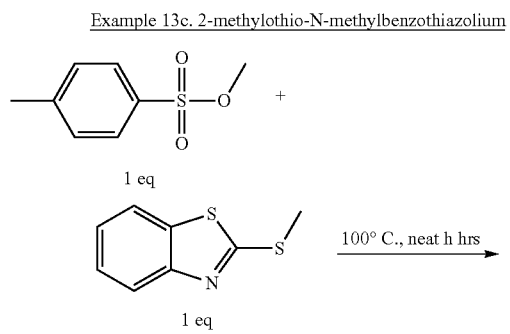

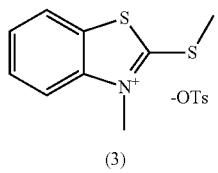

Experimental

Methyl-p-toluenesulfonate (Aldrich, 2.7 mmol, 500 mg) and 2-(Methylthio)benzothiazole (Aldrich, 2.7 mmol, 489 mg) were added together and heated to 100° C. under inert atmosphere. Reaction proceeded for four hours. Isolate product by precipitation with acetone. Reaction monitored by C18 TLC or C18 HPLC. Glazer et al. *Nuc. Acids Res.* 20(1992) 2803-2812 Brooker et al. *J. Am. Chem. Soc.* 63(1942)199-210

Example 13d. 1-(4-Iodoalkyl)4-[3-methyl-2,3-dihydro-(benzo-1,3-thiazole)-2-methylidene]quinolinium iodide

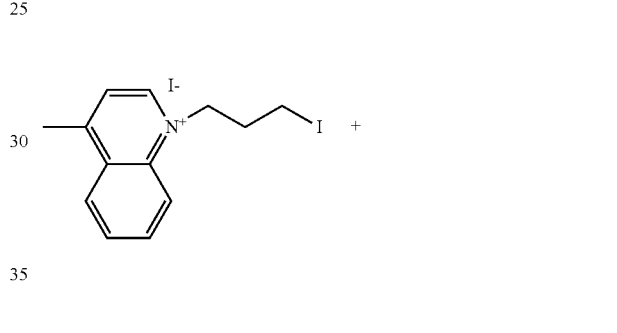

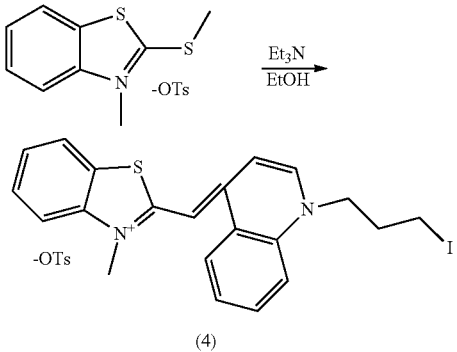

Experimental (2) (0.82 mmol, 300 mg) and (3) (0.82 mmol, 360 mg) are added together in 3 mL ethanol. Solution is heated until reagents are dissolved. Triethylamine (Aldrich, 0.82 mmol, 83 mg) was then added to solution and reaction removed from oil bath and continued to react at room temperature for 30 minutes. Reaction monitored via C18 HPLC. Isolation of product done by using ethyl ether precipitation, then recrystallization from acetone or ethyl ether generating a red powder. Stærk et al. *Bioconj. Chem.* 8(1997)869-877 Brooker et al. *J. Am. Chem. Soc.* 63(1942)199-210

Example 12e. TO-TO acid
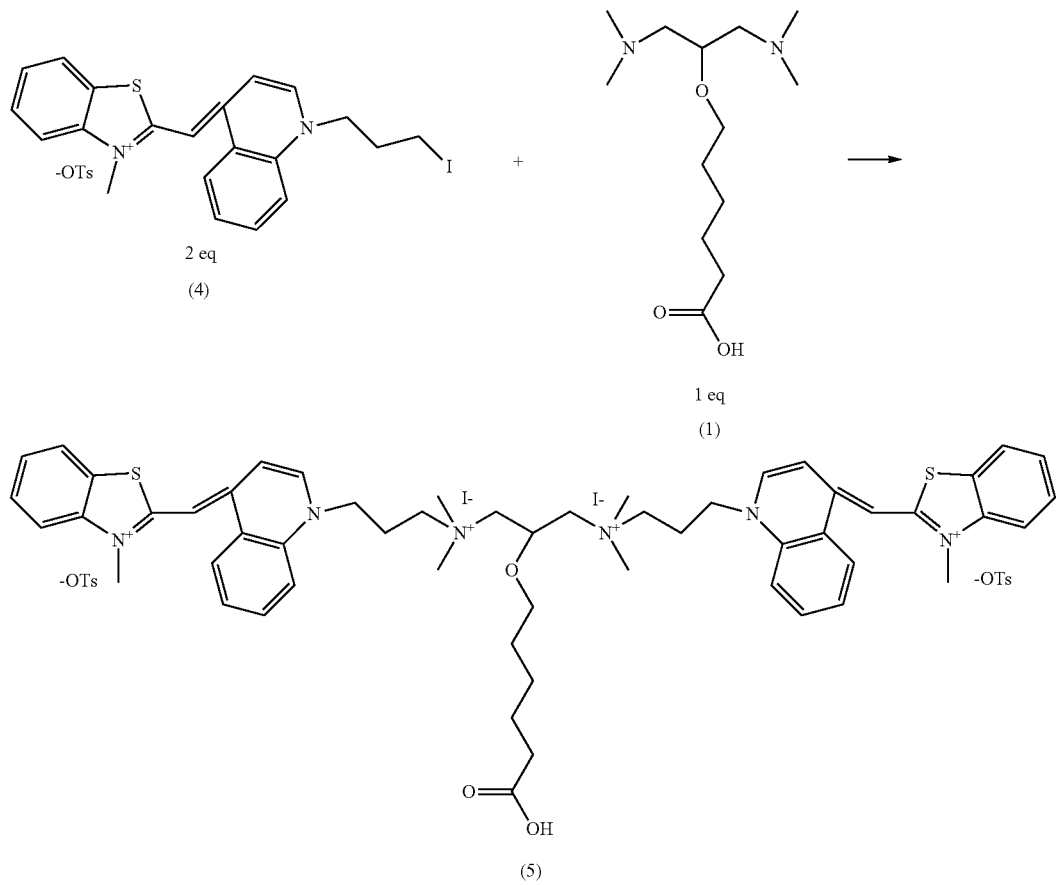
Experimental
(4) (0.4 mmol, 300 mg) and (1) (0.2 mmol, 52 mg) are dissolved in 5 mL anhydrous DMF. Reflux reaction overnight at 155° C. Reaction monitored by C18 HPLC. Product isolated by precipitation in DMF/MeOH mixture, or by C18 chromatography.
Example 12f. TO-TO-NHSE
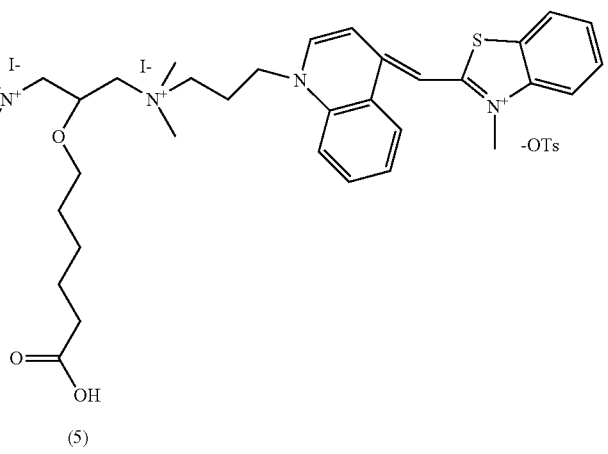

-continued
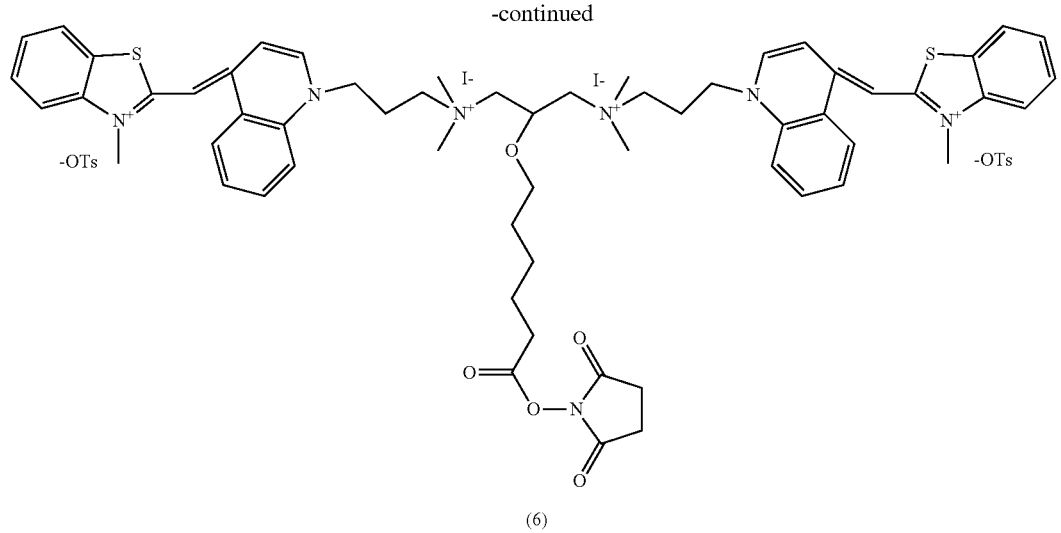
(6)
Experimental
(5) (6.6e-2 mmol, 100 mg) N-hydroxysuccinimide (Aldrich, 0.131 mmol, 15 mg) and 1,3-dicyclohexylcarbodiimide (Aldrich, 0.2 mmol, 41 mg) are added together in 2 mL of anhydrous DMF. Reaction proceeds at room temperature for 2 hours. Reaction monitored by C18 HPLC. Product isolated by precipitation with ethyl ether. Sample is then dried further in vacuo.
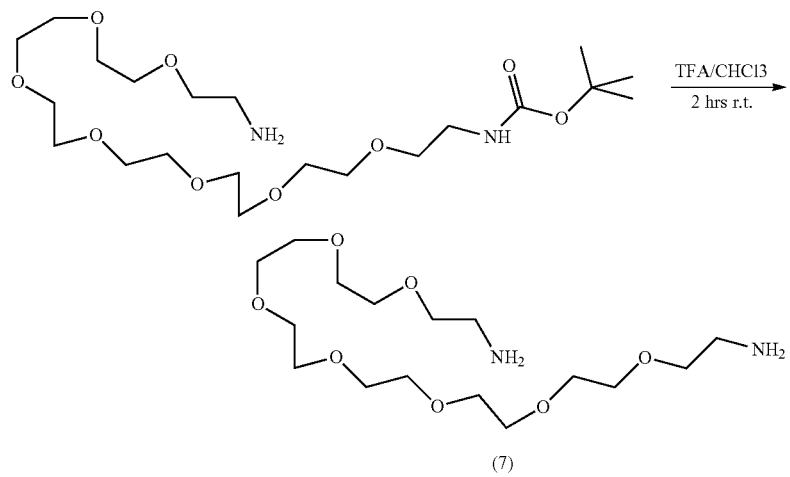
(7)

Experimental:

BOC-amino PEG amine purchased from PolyPure (1 gram), was added to a trifluoroacetic acid/chloroform solution (1:1 v/v, 20 mL). Reaction was stirred at room temperature for 2 hours. NaHCO3 (10 mL, 10 mM) was slowly added to the reaction. The aqueous layer was separated from the organic layer and retained. Chloroform was added and two extractions (20 mL each) were performed. To the aqueous layer, ethyl ether (20 ml) was added and the extraction was performed twice. The aqueous layer was dried in vacu. The final product was a clear oily residue, and weighed approximately 1 gram. Yield was estimated at less than 100% due to possible salts and water still present in sample.

Example 12h. dATP-PEG8-amine

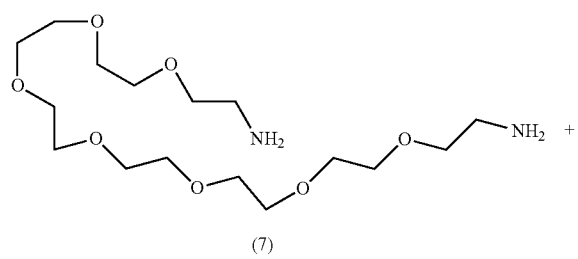

(7)

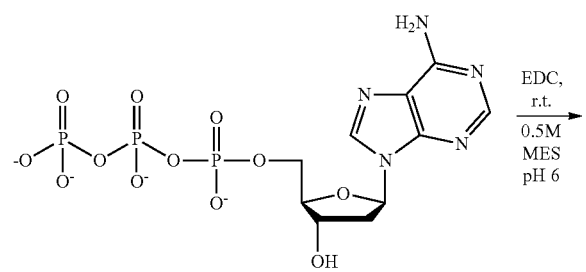

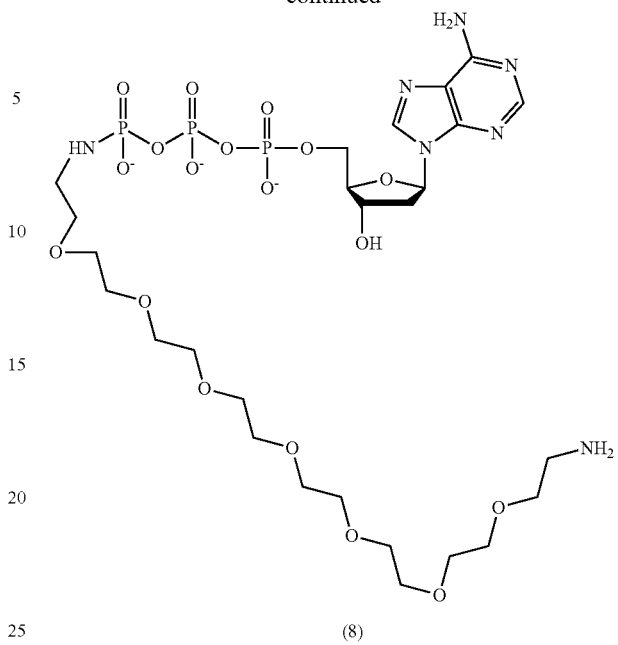

(8)

Experimental:

13.3 mg dATP from Sigma (24.8 µmol, 1 equiv) and 190.6 mg EDC from Aldrich (992 µmol, 40 equiv) were added together in 500 mM MES buffer pH 5.8, resulting in concentrations of 79 mM and 3.2M respectively. The reaction proceeded at room temperature for 10 minutes. A PEG-diamine (7) solution (750 mM, 186 µmol, 7.5 equiv) in 500 mM MES buffer, pH adjusted to 6 with 5M KOH was added to the dATP/EDC (248 uL). The reaction proceeded at room temperature overnight. The large excess of reagents and overnight reaction converted the entire amount of starting material to desired product. The product was first purified on a HiPrep™ DEAE 20 mL column from Amersham with buffer A and B. A: 10 mM phosphate+20% ACN and buffer B: Buffer A in 1M NaCl. LC conditions: 0-10 min 0% B, 10-15 min 0-100% B, 15-20 min 100% B at a flow rate of 10 mL/min. The free PEG eluted from the column in void volume. The nucleotide conjugate product eluted as a broad peak at 5-10 minutes. This broad peak was collected and dried in vacu. The product was further purified on a 30×250 mm 10 um Inertsil ODS-3 column from Varian, with a new buffer system A and B, where buffer A was 100 mM TEAAc (pH 6.6) with 4% ACN and buffer B was 100 mM TEAAc (pH 6.6) with 80% acetonitrile. LC conditions: 0-5 min 0-15% B, 5-10 min 15-20% B, 10-20 min 20-100% B with a flow rate of 20 mL/min. The product that eluted at 12 minutes was collected and then dried in vacu. Yield averages 30% after purification steps.

Example 12i. dATP-PEG8-TOTO
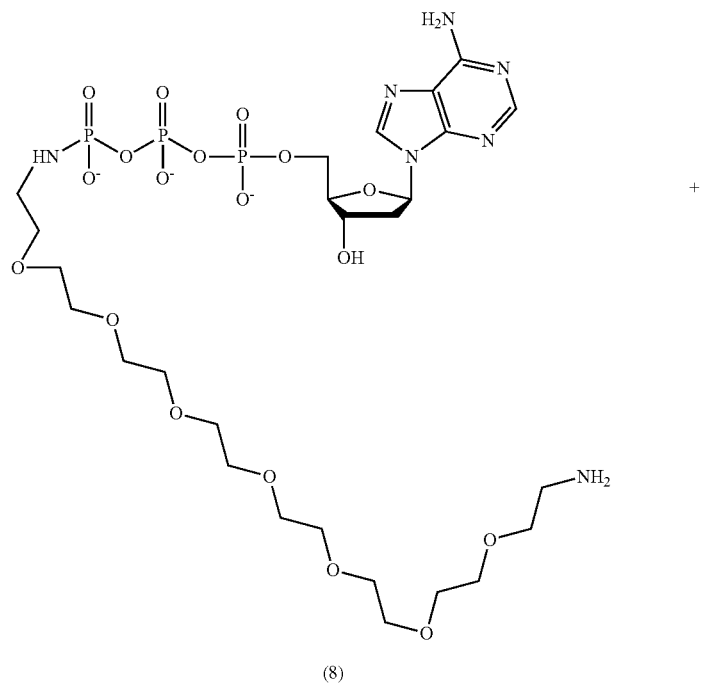
(8)
+
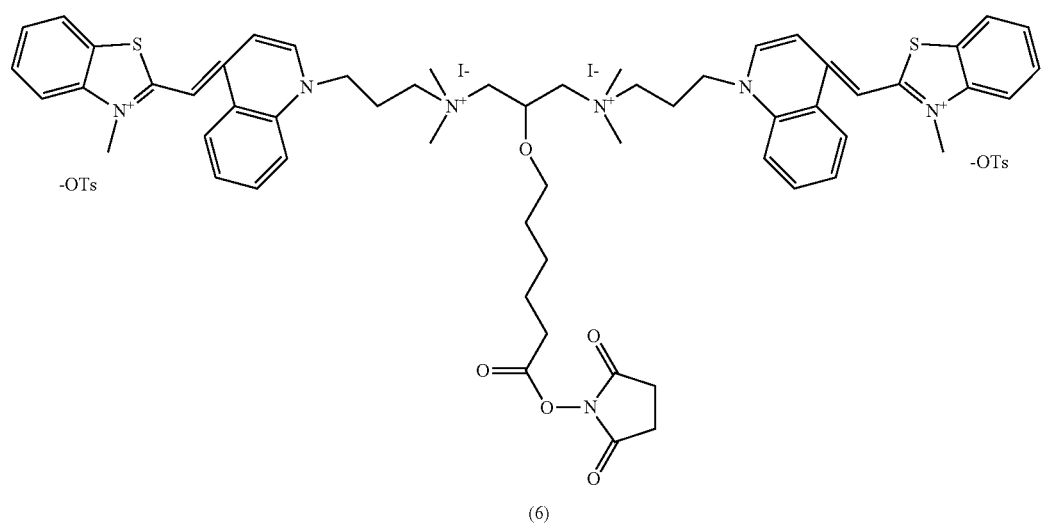
(6)

-continued

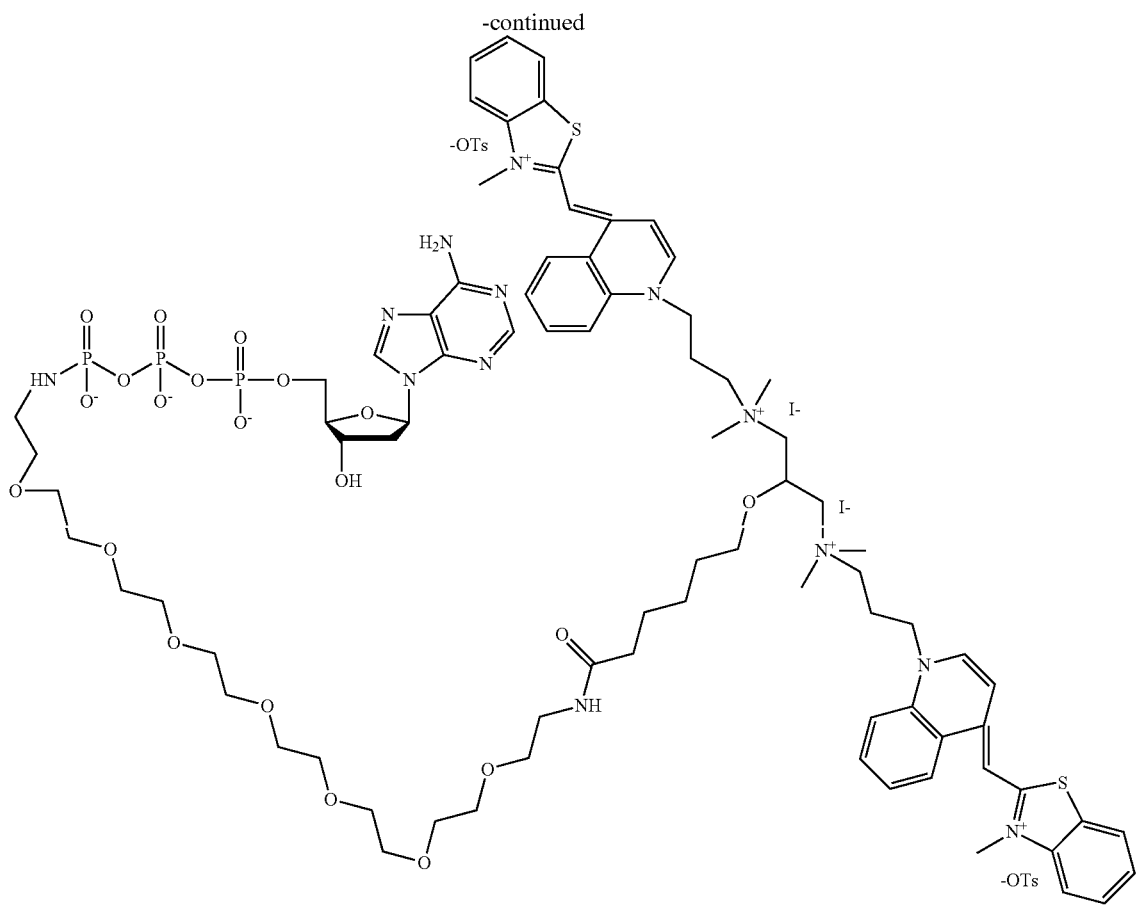

(9)

Experimental:

(8) (4.2e-4 mmol, 42 uL) and (6) (5e-4 mmol, 26.5 uL) are added together as solutions dissolved in 50 mM carbonate buffer pH 8.3. Reaction occurs at room temperature for 3 hours. Purification of desired product is conducted using C18 HPLC. Desired product is collected and dried in vacu.

All publications and patent applications cited in this specification are herein incorporated by reference as if each individual publication or patent application were specifically and individually indicated to be incorporated by reference.

What is claimed is:

1. A compound having Formula I:

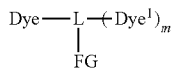

I wherein:
Dye is a monomeric or dimeric dye;
Dye$^1$ is a monomeric dye;
L is a covalent linkage or bridge;
m is 1; and
FG is a bio-moiety comprising the formula:

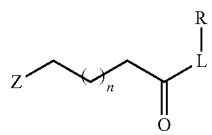

wherein:
n is 0-20;
Z is a member selected from the group consisting of a direct link, O, S, CR$^1$R$^2$, NR$^3$R$^4$, and P(O)$_2$;
R$^1$, R$^2$, R$^3$, and R$^4$ are each members independently selected from the group consisting of H and optionally substituted alkyl;
L is a covalent linkage; and
R is biomolecule.

2. The compound of claim 1, wherein said compound has Formula Ia:

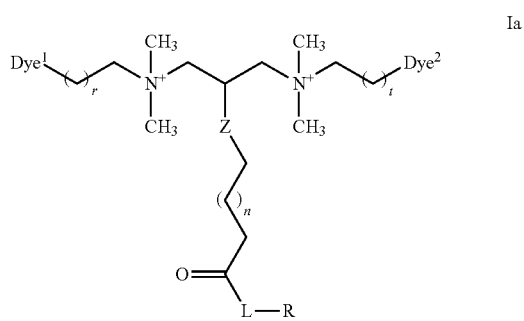

Ia wherein:

Dye[1] is selected from the group consisting of TO-1, TO-3, BO-1, BO-3, YO-1, YO-3, JO-1, JO-3, PO-1, PO-3, LO-1, LO-3, YO-1, YO-3, propidium and psoralen;

Dye[2] is selected from the group consisting of TO-1, TO-3, BO-1, BO-3, YO-1, YO-3, JO-1, JO-3, PO-1, PO-3, LO-1, LO-3, YO-1, YO-3, propidium and psoralen;

r is 1-6;

t is 1-6;

n is 0-20;

Z is a member selected from the group consisting of O, S, $CR^1R^2$, $NR^3R^4$, and $P(O)_2$;

$R^1$, $R^2$, $R^3$, and $R^4$ are each members independently selected from the group consisting of H and optionally substituted alkyl;

L is a member selected from the group consisting of a direct link, or a covalent linkage, wherein said covalent linkage is linear or branched, cyclic or heterocyclic, saturated or unsaturated, having 1-100 atoms selected from the group consisting of C, N, P, O, and S, wherein L can have additional hydrogen atoms to fill valences, and wherein said linkage contains any combination of ether, thioether, amine, ester, carbamate, urea, thiourea, oxy or amide bonds; or single, double, triple or aromatic carbon-carbon bonds; or phosphorus-oxygen, phosphorus-sulfur, nitrogen-nitrogen, nitrogen-oxygen, or nitrogen-platinum bonds; or aromatic or heteroaromatic bonds; and R is biomolecule.

3. The compound of claim 2, wherein Dye[1] and Dye[2] are each members independently selected from the group consisting of BO-1, BO-3, JO-1, LO-1, PO-1, PO-3, TO-1, TO-3, YO-1, YO-3 and psoralen.

4. The compound of claim 2, wherein R is selected from the group consisting of a small molecule, a marker, a cell, a liposome, a protein, a peptide, an enzyme substrate, a hormone, an antibody, an antigen, a hapten, an avidin, a streptavidin, biotin, a carbohydrate, an oligosaccharide, a polysaccharide, a nucleic acid, a deoxy nucleic acid, a fragment of DNA, a fragment of RNA, nucleotide phosphate, acyclo terminator triphosphates, dideoxy terminator triphosphates, and PNA.

5. The compound of claim 2, wherein L is of the formula:

$$-R^1-X^1-Y^1-$$

wherein $R^1$ is a member selected from the group consisting of a O, S or optionally substituted nitrogen and a direct link;

$X^1$ is a member selected from the group consisting of a direct link and $C_2$-$C_{50}$ alkylene optionally interrupted by a heteroatom; and $Y^1$ is a member selected from the group consisting of a direct link, oxygen, an optionally substituted nitrogen and sulfur.

6. The compound of claim 2, wherein Dye[1] is the same as Dye[2].

7. The compound of claim 4, wherein said biomolecule is a nucleotide phosphate selected from the group consisting of a nucleotide monophosphate, di-, tri-, tetra-, penta-, and hexaphosphate.

8. The compound of claim 7, wherein said biomolecule is a nucleotide triphosphate.

9. The compound of claim 2, wherein:

r is 1, 2, 3, 4, 5 or 6;

t is 1, 2, 3, 4, 5 or 6; and n is 4, 5, 5, 6, 7, 8, 9, 10, 11, or 12.

10. The compound of claim 2, wherein:

$R^1$ is nitrogen;

$X^1$ is $(OCH_2CH_2)_{1-25}$; and $Y^1$ is nitrogen.

11. The compound of claim 7, wherein said compound has the formula:

12. A compound of claim 7, wherein said compound has the formula:
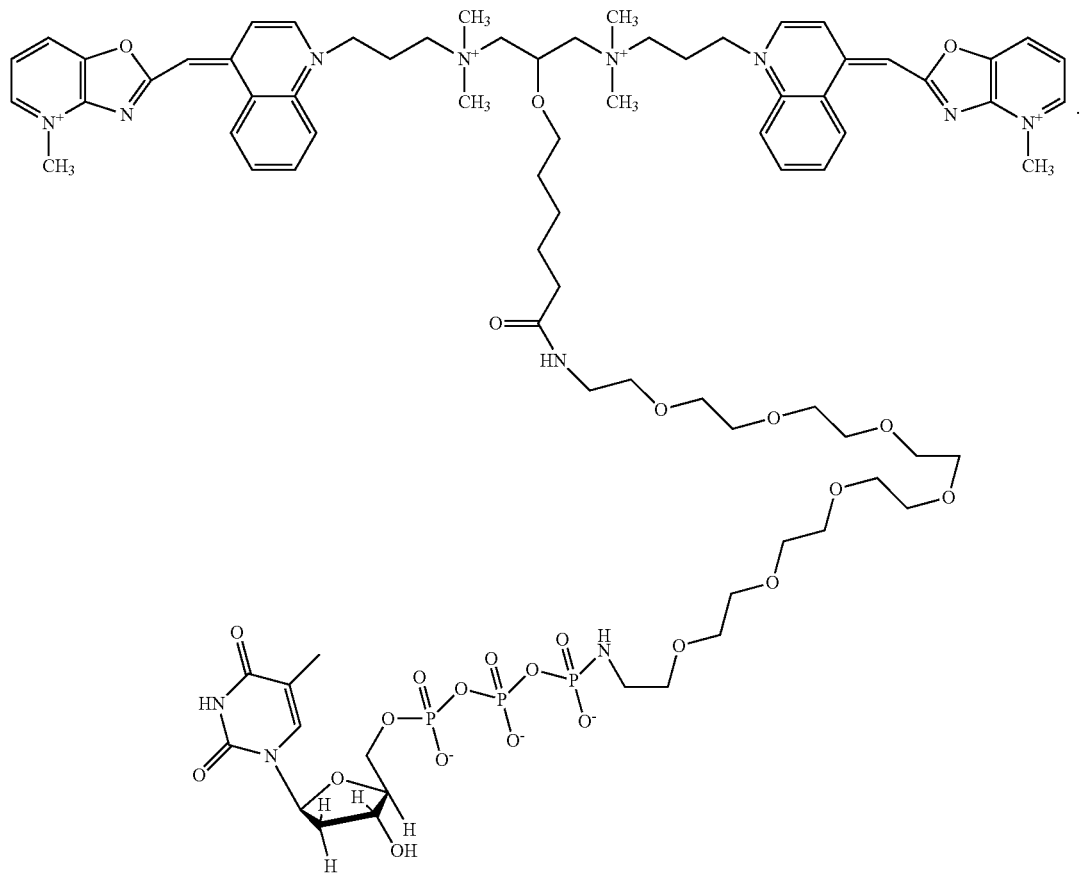
* * * * *

SEQUENCE LISTING

<160> NUMBER OF SEQ ID NOS: 39

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence:DNA
      nanoparticle StartA 40-mer

<400> SEQUENCE: 1
cggacgcaaa gcatgcaccc agccaaattc acaaggcgat                    40

<210> SEQ ID NO 2
<211> LENGTH: 41
<212> TYPE: DNA
<213> ORGANISM: Artificial Sequence
<220> FEATURE:

-continued

```
<223> OTHER INFORMATION: Description of Artificial Sequence:DNA
      nanoparticle StartB 41-mer

<400> SEQUENCE: 2
gaccacgcca cccgcctagc cgtataacga agcgaacaac g                          41

<210> SEQ ID NO 3
<211> LENGTH: 170
<212> TYPE: DNA
<213> ORGANISM: Artificial Sequence
<220> FEATURE:
<223> OTHER INFORMATION: Description of Artificial Sequence:DNA
      nanoparticle Ring1 170-mer oligonucleotide

<400> SEQUENCE: 3
aatcaacaaa gtcaccagga tcacacggca aatacatagg cttttcgttg ttcgcttcgt      60
tatacggcta ggcgggtggc gtggtcatcg ccttgtgaat ttggctgggt gcatgctttg     120
cgtccgtttt atcgatgtag tctgaaatga acatgagcaa tcgaggcgcg                170

<210> SEQ ID NO 4
<211> LENGTH: 170
<212> TYPE: DNA
<213> ORGANISM: Artificial Sequence
<220> FEATURE:
<223> OTHER INFORMATION: Description of Artificial Sequence:DNA
      nanoparticle Ring2 170-mer oligonucleotide

<400> SEQUENCE: 4
agataagaca acacaacttg aggtccatct agcaactcaa gttttgccta tgtatttgcc      60
gtgtgatcct ggtgactttg ttgattcgcg cctcgattgc tcatgttcat ttcagactac     120
atcgattttt cgcggcattc agctggacca tgggcgctac aatcacctac                170

<210> SEQ ID NO 5
<211> LENGTH: 170
<212> TYPE: DNA
<213> ORGANISM: Artificial Sequence
<220> FEATURE:
<223> OTHER INFORMATION: Description of Artificial Sequence:DNA
      nanoparticle Ring3 170-mer oligonucleotide

<400> SEQUENCE: 5
cacgagctgt aataaatagc gtatccaaat gctaacttat attttcttga gttgctagat      60
ggacctcaag ttgtgttgtc ttatctgtag gtgattgtag cgcccatggt ccagctgaat     120
gccgcgtttt acccaataac accgagatcg cccgtaaggt ctagtcatat                170

<210> SEQ ID NO 6
<211> LENGTH: 170
<212> TYPE: DNA
<213> ORGANISM: Artificial Sequence
<220> FEATURE:
<223> OTHER INFORMATION: Description of Artificial Sequence:DNA
      nanoparticle Ring4 170-mer oligonucleotide

<400> SEQUENCE: 6
accgcagaac tatgagtaga acggacagct cgagatgaat cttttataa gttagcattt       60 ggatacgcta tttattacag ctcgtgatat gactagacct tacgggcgat ctcggtgtta     120
ttgggttttt atgacgaacg cgataaggca ttaaatgtcc cgttgccata                170

<210> SEQ ID NO 7
<211> LENGTH: 170
<212> TYPE: DNA
<213> ORGANISM: Artificial Sequence
```

```
<220> FEATURE:
<223> OTHER INFORMATION: Description of Artificial Sequence:DNA
      nanoparticle Ring5 170-mer oligonucleotide

<400> SEQUENCE: 7
catatgccga aatggccagg taggattacg acgactatcg attttgattc atctcgagct    60
gtccgttcta ctcatagttc tgcggttatg gcaacgggac atttaatgcc ttatcgcgtt   120
cgtcattttt catcggccac aggaccctgt ccactagcga gtcgaattaa              170

<210> SEQ ID NO 8
<211> LENGTH: 170
<212> TYPE: DNA
<213> ORGANISM: Artificial Sequence
<220> FEATURE:
<223> OTHER INFORMATION: Description of Artificial Sequence:DNA
      nanoparticle Ring6 170-mer oligonucleotide

<400> SEQUENCE: 8
ccgaccgatg gtaaagttag aatgtacatt ggatgcccag attttttcgat agtcgtcgta   60 atcctacctg gccatttcgg catatgttaa ttcgactcgc tagtggacag ggtcctgtgg  120
ccgatgtttt aacgagactg ataactgtac gcgcattgca aacgcacagt              170

<210> SEQ ID NO 9
<211> LENGTH: 170
<212> TYPE: DNA
<213> ORGANISM: Artificial Sequence
<220> FEATURE:
<223> OTHER INFORMATION: Description of Artificial Sequence:DNA
      nanoparticle Ring7 170-mer oligonucleotide

<400> SEQUENCE: 9
tcatgatgga gtaccgaacc atatagccag gtgcacggaa cttttctgg gcatccaatg     60 tacattctaa ctttaccatc ggtcggactg tgcgtttgca atgcgcgtac agttatcagt   120
ctcgtttttt cagagtggac ttaaactcgg cggcgaccat ctcaatgtga              170

<210> SEQ ID NO 10
<211> LENGTH: 170
<212> TYPE: DNA
<213> ORGANISM: Artificial Sequence
<220> FEATURE:
<223> OTHER INFORMATION: Description of Artificial Sequence:DNA
      nanoparticle Ring8 170-mer oligonucleotide

<400> SEQUENCE: 10
aacgctcact tagatacaaa ctgacaatgc gactggaata cttttgttcc gtgcacctgg    60
ctatatggtt cggtactcca tcatgatcac attgagatgg tcgccgccga gtttaagtcc   120
actctgtttt cgacaaatta gactcacagc gtcagtgaca gttccatacc              170

<210> SEQ ID NO 11
<211> LENGTH: 81
<212> TYPE: DNA
<213> ORGANISM: Artificial Sequence
<220> FEATURE:
<223> OTHER INFORMATION: Description of Artificial Sequence:DNA
      nanoparticle 81-mer End

<400> SEQUENCE: 11
gctgtttaat ctgagtgtcg cagtcactgt caaggtatgg ttgcgagtga atctatgttt    60
gactgttacg ctgaccttat g                                              81

<210> SEQ ID NO 12
```

-continued

```
<211> LENGTH: 88
<212> TYPE: DNA
<213> ORGANISM: Artificial Sequence
<220> FEATURE:
<223> OTHER INFORMATION: Description of Artificial Sequence:individual
      sequenced molecule in microtiter plate well

<400> SEQUENCE: 12
tatgaaaatt ttccggttta aggcgtttcc gttcttcttc gtcataactt aatgtttta        60 tttaaatacc ctctgaaaag aaaggaaa                                          88

<210> SEQ ID NO 13
<211> LENGTH: 88
<212> TYPE: DNA
<213> ORGANISM: Artificial Sequence
<220> FEATURE:
<223> OTHER INFORMATION: Description of Artificial Sequence:individual
      sequenced molecule in microtiter plate well

<400> SEQUENCE: 13
cgacaggtgc tgaaagcgag gcttttggc ctctgtcgtt cctttctct gttttgtcc          60 gtgratgaac aatggaagtc aacaaaaa                                          88

<210> SEQ ID NO 14
<211> LENGTH: 88
<212> TYPE: DNA
<213> ORGANISM: Artificial Sequence
<220> FEATURE:
<223> OTHER INFORMATION: Description of Artificial Sequence:individual
      sequenced molecule in microtiter plate well

<400> SEQUENCE: 14
gcagctggct gacattttcg gtgcgagtat ccgtaccatt cagaactggc aggaacaggg        60
aatsccgttc tgcgaggcgg tggcaagg                                          88

<210> SEQ ID NO 15
<211> LENGTH: 88
<212> TYPE: DNA
<213> ORGANISM: Artificial Sequence
<220> FEATURE:
<223> OTHER INFORMATION: Description of Artificial Sequence:individual
      sequenced molecule in microtiter plate well

<400> SEQUENCE: 15
gtaatgaggt gctttatgac tctgccgccg tcataaaatg gtatgccgaa agggatgctg        60
aaatgagaac gaaaagctgc gccgggag                                          88

<210> SEQ ID NO 16
<211> LENGTH: 21
<212> TYPE: PRT
<213> ORGANISM: Artificial Sequence
<220> FEATURE:
<223> OTHER INFORMATION: Description of Artificial Sequence:amino acid
      anchor
<220> FEATURE:
<221> NAME/KEY: MOD_RES
<222> LOCATION: (11)
<223> OTHER INFORMATION: Xaa = p-acetyl-L-phenylalanine (pa-Phe)

<400> SEQUENCE: 16

Leu Leu Ser Lys Lys Arg Ser Leu Cys Cys Xaa Cys Thr Val Ile Val
 1               5                  10                  15

Tyr Val Thr Asp Thr
            20
```

```
<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:
      double-stranded oligonucleotide first adaptor
<220> FEATURE:
<221> NAME/KEY: modified_base
<222> LOCATION: (1)
<223> OTHER INFORMATION: n = c modified by Biotin

<400> SEQUENCE: 17
ngccacatta cacttcctaa cacgt                                            25

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:
      double-stranded oligonucleotide first adaptor

<400> SEQUENCE: 18
cgtgttagga agtgtaatgt ggcg                                             24

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence:
      double-stranded oligonucleotide second adaptor

<400> SEQUENCE: 19
cagtaggtag tcaaggctag agtct                                            25

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence:
      double-stranded oligonucleotide second adaptor

<400> SEQUENCE: 20
gactctagcc ttgactacct actg                                             24

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence:ligated DNA
      product 1 and product 2 adaptor and genomic DNA
<220> FEATURE:
<221> NAME/KEY: modified_base
<222> LOCATION: (1)
<223> OTHER INFORMATION: n = c modified by Biotin
<220> FEATURE:
<221> NAME/KEY: modified_base
<222> LOCATION: (26)..(30)
<223> OTHER INFORMATION: n = g, a, c or t (genomic DNA)

<400> SEQUENCE: 21
ngccacatta cacttcctaa cacgtnnnnn                                       30

<210> SEQ ID NO 22
<211> LENGTH: 33
<212> TYPE: DNA
```

```
<213> ORGANISM: Artificial Sequence
<220> FEATURE:
<223> OTHER INFORMATION: Description of Artificial Sequence:ligated DNA
      product 1 and product 3 adaptor and genomic DNA
<220> FEATURE:
<221> NAME/KEY: modified_base
<222> LOCATION: (1)..(5)
<223> OTHER INFORMATION: n = g, a, c or t (genomic DNA)

<400> SEQUENCE: 22
nnnnnagact ctagccttga ctacctactg aaa                                      33

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence:ligated DNA
      product 1 and product 3 adaptor and genomic DNA
<220> FEATURE:
<221> NAME/KEY: modified_base
<222> LOCATION: (1)
<223> OTHER INFORMATION: n = c modified by 5'-phosphate
<220> FEATURE:
<221> NAME/KEY: modified_base
<222> LOCATION: (26)..(30)
<223> OTHER INFORMATION: n = g, a, c or t (genomic DNA)

<400> SEQUENCE: 23
nagtaggtag tcaaggctag agtctnnnnn                                          30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence:ligated DNA
      product 1 and product 2 adaptor and genomic DNA
<220> FEATURE:
<221> NAME/KEY: modified_base
<222> LOCATION: (1)..(5)
<223> OTHER INFORMATION: n = g, a, c or t (genomic DNA)

<400> SEQUENCE: 24
nnnnnacgtg ttaggaagtg taatgtggcg                                          30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence:ligated DNA
      product 2 adaptor and genomic DNA
<220> FEATURE:
<221> NAME/KEY: modified_base
<222> LOCATION: (1)..(5)
<223> OTHER INFORMATION: n = g, a, c or t (genomic DNA)

<400> SEQUENCE: 25
nnnnnacgtg ttaggaagtg taatgtggcg                                          30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence:ligated DNA
      product 2 adaptor and genomic DNA
<220> FEATURE:
<221> NAME/KEY: modified_base
<222> LOCATION: (1)
<223> OTHER INFORMATION: n = c modified by Biotin
```

```
<220> FEATURE:
<221> NAME/KEY: modified_base
<222> LOCATION: (26)..(30)
<223> OTHER INFORMATION: n = g, a, c or t (genomic DNA)

<400> SEQUENCE: 26
ngccacatta cacttcctaa cacgtnnnnn                                          30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence:ligated DNA
      product 3 adaptor and genomic DNA
<220> FEATURE:
<221> NAME/KEY: modified_base
<222> LOCATION: (1)
<223> OTHER INFORMATION: n = c modified by 5'-phosphate
<220> FEATURE:
<221> NAME/KEY: modified_base
<222> LOCATION: (26)..(30)
<223> OTHER INFORMATION: n = g, a, c or t (genomic DNA)

<400> SEQUENCE: 27
nagtaggtag tcaaggctag agtctnnnnn                                          30

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence:ligated DNA
      product 3 adaptor and genomic DNA
<220> FEATURE:
<221> NAME/KEY: modified_base
<222> LOCATION: (1)..(5)
<223> OTHER INFORMATION: n = g, a, c or t (genomic DNA)

<400> SEQUENCE: 28
nnnnnagact ctagccttga ctacctactg aaa                                      33

<210> SEQ ID NO 29
<211> LENGTH: 59
<212> TYPE: DNA
<213> ORGANISM: Artificial Sequence
<220> FEATURE:
<223> OTHER INFORMATION: Description of Artificial Sequence:primed
      circular template
<220> FEATURE:
<221> NAME/KEY: modified_base
<222> LOCATION: (1)..(5)
<223> OTHER INFORMATION: n = g, a, c or t
<220> FEATURE:
<221> NAME/KEY: modified_base
<222> LOCATION: (55)..(59)
<223> OTHER INFORMATION: n = g, a, c or t

<400> SEQUENCE: 29
nnnnncgtgt taggaagtgt aatgtggcgc agtaggtagt caaggctaga gtctnnnnn          59

<210> SEQ ID NO 30
<211> LENGTH: 49
<212> TYPE: DNA
<213> ORGANISM: Artificial Sequence
<220> FEATURE:
<223> OTHER INFORMATION: Description of Artificial Sequence:primer oligo
      complementary to both adaptors

<400> SEQUENCE: 30
agactctagc cttgactacc tactgcgcca cattacactt cctaacacg                     49
```

```
<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence:
      amplification forward primer

<400> SEQUENCE: 31
atgatcgttt ctgccatcgc agctaac                                            27

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence:
      amplification reverse primer

<400> SEQUENCE: 32
tcagtggcaa atcgcc                                                        16

<210> SEQ ID NO 33
<211> LENGTH: 75
<212> TYPE: DNA
<213> ORGANISM: Artificial Sequence
<220> FEATURE:
<223> OTHER INFORMATION: Description of Artificial Sequence:synthetic
      oligonucleotide encoding Strep-Tag II sequence
      overlapping 5'-end of amplified T7 exo-polymerase
      gene

<400> SEQUENCE: 33
atgtccaact ggtcccaccc gcagttcgaa aaaggtggag gttccgctat gatcgtttct        60
gccatcgcag ctaac                                                         75

<210> SEQ ID NO 34
<211> LENGTH: 25
<212> TYPE: PRT
<213> ORGANISM: Artificial Sequence
<220> FEATURE:
<223> OTHER INFORMATION: Description of Artificial Sequence:Strep-Tag II
      peptide sequence overlapping 5'-end of amplified
      T7 exo-polymerase N-terminus

<400> SEQUENCE: 34

Met Ser Asn Trp Ser His Pro Gln Phe Glu Lys Gly Gly Gly Ser Ala
1               5                   10                  15

Met Ile Val Ser Ala Ile Ala Ala Asn
            20                  25

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence:overlapping
      PCR StepTag forward primer

<400> SEQUENCE: 35
atgtccaact ggtcccaccc                                                    20

<210> SEQ ID NO 36
<211> LENGTH: 16
<212> TYPE: DNA
<213> ORGANISM: Artificial Sequence
```

-continued

```
<220> FEATURE:
<223> OTHER INFORMATION: Description of Artificial Sequence:overlapping
      PCR StepTag reverse primer

<400> SEQUENCE: 36
tcagtggcaa atcgcc                                                        16

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence:normal
      allele and (delta)F508 deletion mutant synthetic
      oligonucleotide primer derived from cystic
      fibrosis transmembrane conductance regulator gene

<400> SEQUENCE: 37
tactataaaa gaaattacca c                                                  21

<210> SEQ ID NO 38
<211> LENGTH: 22
<212> TYPE: RNA
<213> ORGANISM: Artificial Sequence
<220> FEATURE:
<223> OTHER INFORMATION: Description of Artificial Sequence:cystic
      fibrosis transmembrane conductance regulator gene normal
      allele template

<400> SEQUENCE: 38
gugguaauuu cuuuuauagu ag                                                 22

<210> SEQ ID NO 39
<211> LENGTH: 22
<212> TYPE: RNA
<213> ORGANISM: Artificial Sequence
<220> FEATURE:
<223> OTHER INFORMATION: Description of Artificial Sequence:cystic
      fibrosis transmembrane conductance regulator gene
      (delta)F508 mutant allele template

<400> SEQUENCE: 39
gugguaauuu cuuuuauagu aa                                                 22
```